US012781165B2

(12) United States Patent
Tanabe et al.

(10) Patent No.: US 12,781,165 B2
(45) Date of Patent: Nov. 3, 2026

(54) CELL CULTURE DEVICE

(71) Applicants: I Peace, Inc., Palo Alto, CA (US); FANUC CORPORATION, Yamanashi (JP)

(72) Inventors: Koji Tanabe, Palo Alto, CA (US); Ryoji Hiraide, Kyoto (JP); Kazunori Ban, Yamanashi (JP); Satoshi Kinoshita, Yamanashi (JP)

(73) Assignees: Peace, Inc., Palo Alto, CA (US); FANUC CORPROATION, Yamanashi (JP)

( * ) Notice: Subject to any disclaimer, the term of this patent is extended or adjusted under 35 U.S.C. 154(b) by 863 days.

(21) Appl. No.: 17/775,205

(22) PCT Filed: Oct. 30, 2020

(86) PCT No.: PCT/JP2020/040785
§ 371 (c)(1),
(2) Date: May 6, 2022

(87) PCT Pub. No.: WO2021/090767
PCT Pub. Date: May 14, 2021

(65) Prior Publication Data
US 2022/0403307 A1 Dec. 22, 2022

Related U.S. Application Data
(60) Provisional application No. 62/931,471, filed on Nov. 6, 2019.

(51) Int. Cl.
*C12M 1/00* (2006.01)
*C12M 1/04* (2006.01)
*C12M 3/00* (2006.01)

(52) U.S. Cl.
CPC .............. *C12M 3/00* (2013.01); *C12M 23/24* (2013.01)

(58) Field of Classification Search
CPC .............................. C12M 23/00; C12M 29/00
See application file for complete search history.

(56) References Cited

U.S. PATENT DOCUMENTS

2009/0137026 A1* 5/2009 Kobayashi ............ C12M 41/00 435/286.4
2011/0003380 A1* 1/2011 Miltenyi ................ B04B 13/00 494/67

(Continued)

FOREIGN PATENT DOCUMENTS

CN 103667054 A 3/2014
CN 110129365 A 8/2019

(Continued)

OTHER PUBLICATIONS

English language translation of WO 2018/154788 to Suto et al, generated 2025.*

(Continued)

*Primary Examiner* — Nathan A Bowers
(74) *Attorney, Agent, or Firm* — Studebaker Brackett PLLC

(57) ABSTRACT

A cell culture device (200) includes a cell culture vessel (22) for culturing cells, a factor container (81) for storing a factor, a reagent container (82) for storing a reagent for introducing the factor into the cells, and a flow path for transporting the factor and the reagent from the factor container (81) and the reagent container (82) to the cell culture vessel (22).

17 Claims, 15 Drawing Sheets

(56) References Cited

U.S. PATENT DOCUMENTS

| | | | | |
|---|---|---|---|---|
| 2015/0306641 | A1 | 10/2015 | Suzuki et al. | |
| 2018/0273891 | A1 | 9/2018 | Tanabe et al. | |
| 2019/0382706 | A1 | 12/2019 | Tanabe et al. | |
| 2020/0032197 | A1* | 1/2020 | Guest | C12M 45/22 |
| 2020/0165557 | A1* | 5/2020 | Lesch | C12P 21/02 |
| 2020/0255790 | A1* | 8/2020 | Veraitch | C12M 37/04 |
| 2021/0047602 | A1* | 2/2021 | Vang | C12M 35/08 |
| 2021/0284948 | A1* | 9/2021 | Hauwaerts | A61K 40/11 |

FOREIGN PATENT DOCUMENTS

| | | | |
|---|---|---|---|
| JP | 4183742 | B1 | 11/2008 |
| JP | 2014-114997 | A | 6/2014 |
| JP | 2018-526992 | A | 9/2018 |
| JP | 2019-080575 | A | 5/2019 |
| WO | 2018/154788 | A1 | 8/2018 |

OTHER PUBLICATIONS

International Search Report issued in PCT/JP2020/040785; mailed Dec. 28, 2020.

International Preliminary Report On Patentability (Chapter II) with ANNEX issued in PCT/JP2020/040785; completed Feb. 16, 2022.

* cited by examiner (a)

(b)

(a) (b)

CELL CULTURE DEVICE

TECHNICAL FIELD

The present invention relates to a cell technology, and relates to a cell culture device.

BACKGROUND ART

Embryonic stem cells (ES cells) are stem cells derived from early human or mouse embryos. ES cells have pluripotency that allows them to differentiate into any type of cells in a living body. Currently, human ES cells can be used for cell transplantation therapy for numerous diseases such as Parkinson's disease, juvenile diabetes, and leukemia. However, there are also obstacles to ES cell transplantation. In particular, ES cell transplantation can elicit immunorejection similar to a rejection response that follows unsuccessful organ transplantation. In addition, there are many criticisms and dissenting opinions from a moral point of view regarding use of ES cells derived by destroying human embryos.

Under such circumstances, Professor Shinya Yamanaka at Kyoto University succeeded in deriving induced pluripotent stem cells (iPS cells) by introducing four genes: OCT3/4, KLF4, c-MYC, and SOX2 into somatic cells. For this, Professor Yamanaka was awarded the 2012 Nobel Prize in Physiology or Medicine (for example, refer to Patent Documents 1 and 2). iPS cells are ideal pluripotent cells without rejection responses or moral issues. Therefore, iPS cells are expected to be used for cell transplantation therapy.

CITATION LIST

Patent Document

Patent Document 1: Japanese Patent No. 4183742
Patent Document 2: Patent Publication JP-A 2014-114997

SUMMARY

Technical Problem iPS cells are produced by introducing a reprogramming factor into somatic cells. Not being limited to production of iPS cells, techniques of introducing a factor into cells can be used for various applications. For example, when differentiated cells are produced, a differentiation factor is introduced into stem cells such as iPS cells. When gene editing is performed, a Cas9 protein is introduced into cells. When lentiviruses are produced, a lentivirus vector is introduced into cells. Therefore, one objective of the present invention is to provide a cell culture device in which a factor can be easily introduced into cells.

Solution to Problem

According to an aspect of the present invention, there is provided a cell culture device including a cell culture vessel for culturing cells; a factor container for storing a factor; a reagent container for storing a reagent for introducing the factor into the cells; and a flow path for transporting the factor and the reagent from the factor container and the reagent container to the cell culture vessel.

The cell culture device may further include a mixing tank provided in the flow path for mixing the factor and the reagent.

The cell culture device may further include a first fluid machine for transporting the factor from the factor container to the mixing tank.

In the cell culture device, the first fluid machine may include a pump head and a drive unit for driving the pump head, the flow path may be provided on a substrate, the pump head may be in contact with the flow path, and the drive unit may be removable from the substrate.

In the cell culture device, the first fluid machine may quantitatively transport the factor from the factor container to the mixing tank.

The cell culture device may further include a second fluid machine for transporting the reagent from the reagent container to the mixing tank.

In the cell culture device, the second fluid machine may include a pump head and a drive unit for driving the pump head, the flow path may be provided on a substrate, the pump head may be in contact with the flow path, and the drive unit may be removable from the substrate.

In the cell culture device, the second fluid machine may quantitatively transport the reagent from the reagent container to the mixing tank.

The cell culture device may further include a third fluid machine for transporting a reagent and a factor from the mixing tank to the cell culture vessel.

In the cell culture device, the third fluid machine may quantitatively transport the reagent and the factor from the mixing tank to the cell culture vessel.

In the cell culture device, the third fluid machine may include a pump head and a drive unit for driving the pump head, the flow path may be provided on a substrate, the pump head may be in contact with the flow path, and the drive unit may be removable from the substrate.

In the cell culture device, the third fluid machine may transport the reagent and the factor from the mixing tank to the cell culture vessel a predetermined number of times.

In the cell culture device, the third fluid machine may transport the reagent and the factor from the mixing tank to the cell culture vessel at a predetermined timing.

The cell culture device may further include a diluting solution container for storing a diluting solution and a factor diluting container provided in the flow path for diluting the factor with the diluting solution.

The cell culture device may further include a fourth fluid machine for transporting the diluting solution from the diluting solution container to the factor diluting container.

In the cell culture device, the fourth fluid machine may include a pump head and a drive unit for driving the pump head, the flow path may be provided on a substrate, the pump head may be in contact with the flow path, and the drive unit may be removable from the substrate.

In the cell culture device, the fourth fluid machine may quantitatively transport the diluting solution from the diluting solution container to the factor diluting container.

The cell culture device may further include a diluting solution container for storing a diluting solution and a reagent diluting container provided in the flow path for diluting the reagent with the diluting solution.

The cell culture device may further include a diluting solution container for storing a diluting solution, a factor diluting container provided in the flow path for diluting the factor with the diluting solution, and a reagent diluting container provided in the flow path for diluting the reagent with the diluting solution, and in the mixing tank, the diluted factor and the diluted reagent may be mixed.

The cell culture device may further include a fifth fluid machine for transporting the diluting solution from the diluting solution container to the reagent diluting container.

In the cell culture device, the fifth fluid machine may include a pump head and a drive unit for driving the pump head, the flow path may be provided on a substrate, the pump head may be in contact with the flow path, and the drive unit may be removable from the substrate.

In the cell culture device, the fifth fluid machine may quantitatively transport the diluting solution from the diluting solution container to the reagent diluting container.

The cell culture device may further include a medium container connected to the mixing tank for storing a medium to be supplied to the mixing tank.

The cell culture device may further include a sixth fluid machine for transporting the medium from the medium container to the mixing tank.

In the cell culture device, the sixth fluid machine may include a pump head and a drive unit for driving the pump head, the flow path may be provided on a substrate, the pump head may be in contact with the flow path, and the drive unit may be removable from the substrate.

In the cell culture device, the sixth fluid machine may quantitatively transport the medium from the medium container to the mixing tank.

The cell culture device may further include a plurality of medium containers connected to the mixing tank and each storing a medium to be supplied to the mixing tank.

In the cell culture device, the plurality of medium containers may store different mediums.

In the cell culture device, depending on the number of times the reagent and the factor are transported from the mixing tank to the cell culture vessel, different mediums may be transported from any of the plurality of medium containers to the mixing tank.

In the cell culture device, depending on the timing at which the reagent and the factor are transported from the mixing tank to the cell culture vessel, different mediums may be transported from any of the plurality of medium containers to the mixing tank.

In the cell culture device, an inside of the cell culture vessel, an inside of the factor container, an inside of the reagent container, and an inside of the flow path may be closed from outside air.

In the cell culture device, an inside of the mixing tank may be closed from outside air.

In the cell culture device, an inside of the diluting solution container may be closed from outside air.

In the cell culture device, an inside of the medium container may be closed from outside air.

In the cell culture device, a volume of at least one of the factor container and the reagent container may be variable.

In the cell culture device, a volume of the mixing tank may be variable.

In the cell culture device, a volume of the diluting solution container may be variable.

In the cell culture device, a volume of the medium container may be variable.

In the cell culture device, the factor may be at least one selected from among DNA, RNA, a protein, and a compound.

In the cell culture device, the cell culture vessel, the factor container, the reagent container, and the flow path may be provided on a plate.

Advantageous Effects of Invention

According to the present invention, it is possible to provide a cell culture device in which a factor can be easily introduced into cells.

DESCRIPTION OF EMBODIMENTS

Figure 1:
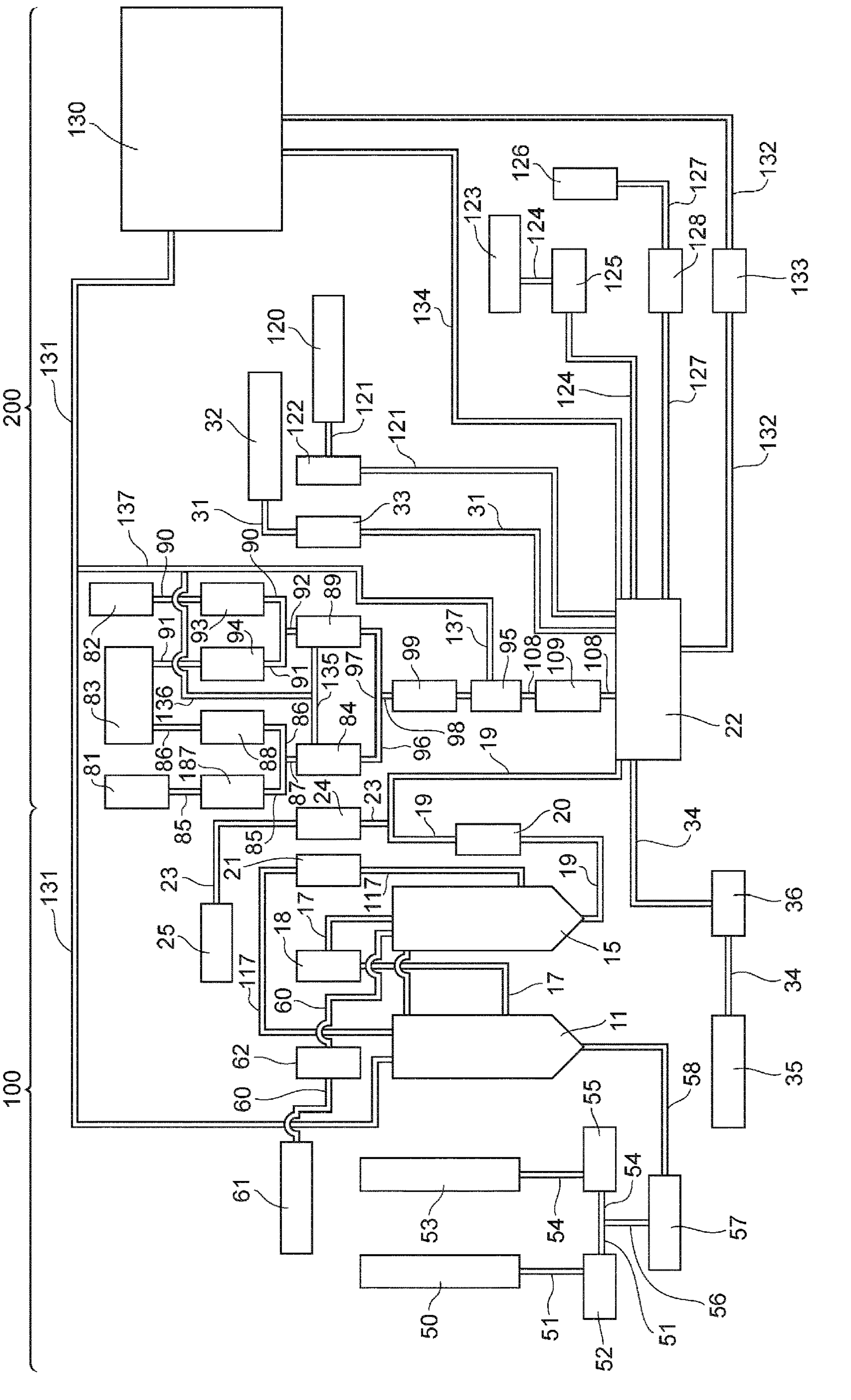
FIG. 1 is a schematic front view of a cell culture system according to an embodiment.

Hereinafter, embodiments of the present invention will be described. In the following description of the drawings, the same or similar parts are denoted with the same or similar reference numerals. However, the drawings are schematic. Therefore, specific sizes and the like should be determined in light of the following description. In addition, it goes without saying that parts may have different relationships and ratios therebetween in each of the drawings.

Figure 2:
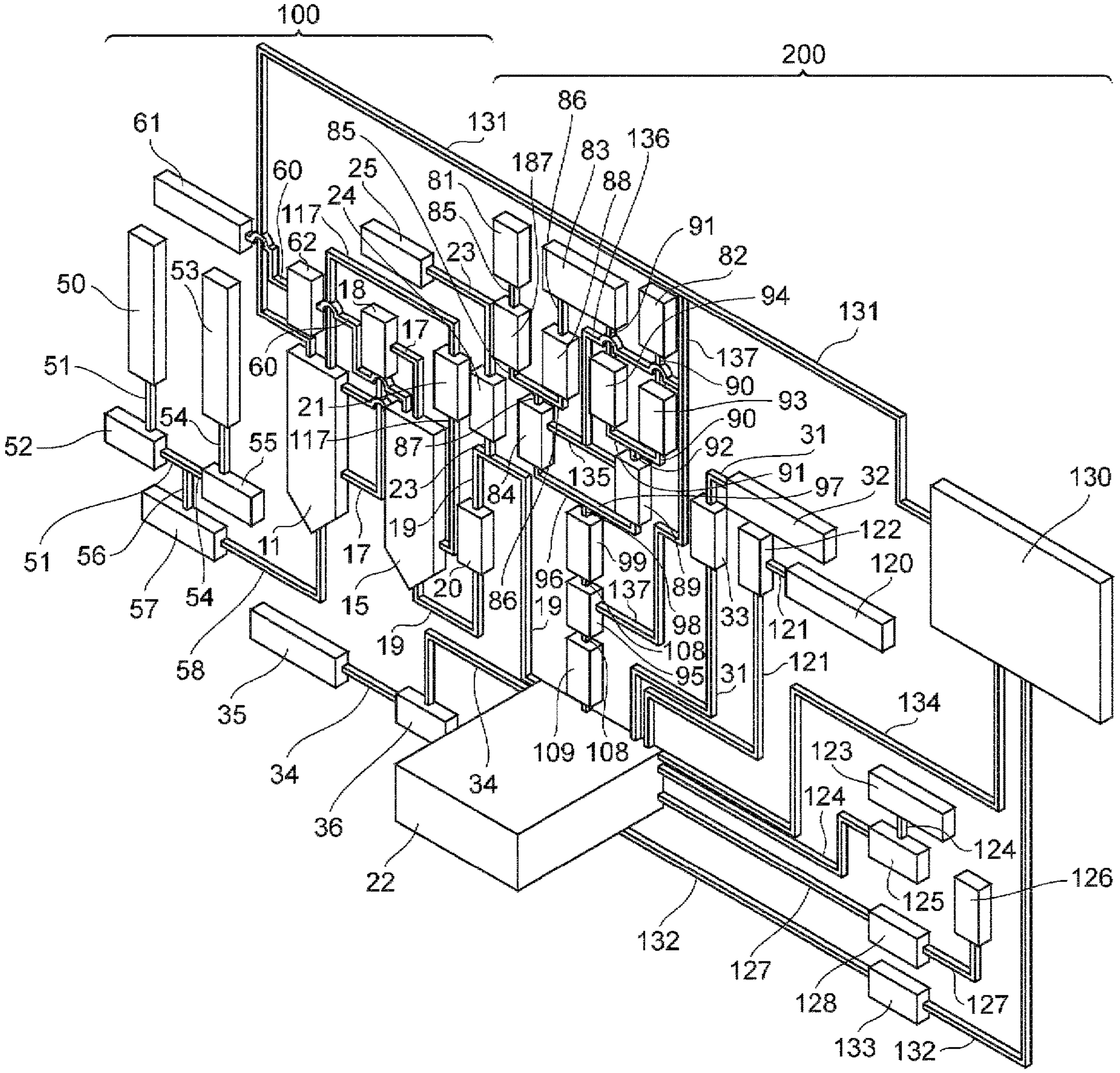
FIG. 2 is a schematic perspective view of a cell culture system according to an embodiment.

As shown in FIG. 1 and FIG. 2, a cell culture device 200 according to an embodiment includes a cell culture vessel 22 for culturing cells, a factor container 81 for storing a factor, a reagent container 82 for storing a reagent for introducing the factor into cells, and flow paths for transporting a factor and a reagent from the factor container 81 and the reagent container 82 into the cell culture vessel 22.

The cell culture device 200 may be connected to, for example, a erythrocyte removal device 100. The erythrocyte removal device 100 includes a blood container 50 for storing blood and a erythrocyte treatment agent container 53 for storing a erythrocyte precipitating agent or a erythrocyte removal agent.

Blood is stored inside the blood container 50. The blood container 50 may have a structure in which the inside can be closed from the outside air. The closed space including the inside of the blood container 50 may have a configuration in which gases, viruses, microorganisms, impurities and the like are not exchanged with the outside. The blood container 50 may be embedded and enclosed in a non-gas-permeable substance. At least a part of the blood container 50 may be provided on a member such as a plate. At least a part of the blood container 50 may be formed by carving into a member. At least a part of the blood container 50 may be carved into a member and formed by superimposing recesses. The blood container 50 can change its volume. In this case, for example, the blood container 50 includes a syringe for storing a fluid and a plunger which is inserted into the syringe and movable in the syringe, and the volume for storing the fluid in the syringe can be changed by moving the plunger. Alternatively, the blood container 50 may be a flexible bellows or bag. Here, in the present disclosure, the fluid includes a gas and a liquid.

A erythrocyte precipitating agent or a erythrocyte removal agent is stored inside the erythrocyte treatment agent container 53. The erythrocyte treatment agent container 53 may have a structure in which the inside can be closed from the outside air. The closed space including the inside of the erythrocyte treatment agent container 53 may have a configuration in which gases, viruses, microorganisms, impurities and the like are not exchanged with the outside. The erythrocyte treatment agent container 53 may be embedded and enclosed in a non-gas-permeable substance. At least a part of the erythrocyte treatment agent container 53 may be provided on a member such as a plate. At least a part of the erythrocyte treatment agent container 53 may be formed by carving into a member. At least a part of the erythrocyte treatment agent container 53 may be carved into a member and formed by superimposing recesses. The erythrocyte treatment agent container 53 can change its volume. In this case, for example, the erythrocyte treatment agent container 53 includes a syringe for storing a fluid and a plunger which is inserted into the syringe and movable in the syringe, and the volume for storing the fluid in the syringe can be changed by moving the plunger. Alternatively, the erythrocyte treatment agent container 53 may be a flexible bellows or bag.

The erythrocyte removal device 100 further includes, for example, a mixer 57 in which the blood and the erythrocyte precipitating agent or the erythrocyte removal agent are mixed. The mixer 57 includes, for example, a bent flow path through which a mixed solution containing the blood and the erythrocyte precipitating agent or the erythrocyte removal agent flows. The bent flow path may be bent in a spiral shape. The flow path may meander in the bent flow path. The cross-sectional area may repeatedly increase and decrease in size in the bent flow path. The mixer 57 may have a structure in which the inside can be closed from the outside air. The closed space including the inside of the mixer 57 may have a configuration in which gases, viruses, microorganisms, impurities and the like are not exchanged with the outside. The mixer 57 may be embedded and enclosed in a non-gas-permeable substance. At least a part of the mixer 57 may be provided on a member such as a plate. At least a part of the mixer 57 may be formed by carving into a member. At least a part of the mixer 57 may be carved into a member and formed by superimposing recesses.

A flow path 51 for transporting at least the blood from the blood container 50 into the mixer 57 is connected to the blood container 50. The blood container 50 and the flow path 51 may be connected by a connector. The connector may be a closed connector in which the inside can be closed. The connector may be an aseptic connector. The connector may be a needleless connector. The needleless connector may be of a split-septum type or a mechanical valve type. The same applies to the other connectors in the present disclosure. A flow path 54 for transporting at least the erythrocyte precipitating agent or the erythrocyte removal agent from the erythrocyte treatment agent container 53 to the mixer 57 is connected to the erythrocyte treatment agent container 53. The erythrocyte treatment agent container 53 and the flow path 54 may be connected by a connector. The flow path 51 and the flow path 54 merge with a flow path 56. The flow path 56 is connected to the mixer 57.

A fluid machine 52 such as a pump for moving the fluid in the flow path 51 may be provided in the flow path 51. A fluid machine 55 such as a pump for moving the fluid in the flow path 54 may be provided in the flow path 54. In the case where a fluid machine is provided in the flow path, a valve other than the fluid machine may not be provided in the flow paths 51 and 54.

A positive displacement pump can be used as the fluid machines 52 and 55. Examples of positive displacement pumps include reciprocating pumps including a piston pump, a plunger pump, and a diaphragm pump, or rotary pumps including a gear pump, a vane pump, and a screw pump. Examples of diaphragm pumps include a tubing pump and a piezoelectric (piezo) pump. The tubing pump may be called a peristaltic pump. In addition, a microfluidic chip module in which various types of pumps are combined may be used. The same applies to other fluid machines in the present disclosure. In the case where a sealable type pump such as a peristaltic pump, a tubing pump, or a diaphragm pump is used, it is possible to transport the fluid without a pump mechanism coming into direct contact with the fluid inside the flow path.

The fluid machines 52 and 55 may include a pump head and a drive unit that drives the pump head. The flow path 51 may be provided on a substrate, the pump head of the fluid machine 52 may be in contact with the flow path 51, and the drive unit of the fluid machine 52 may be removable from the substrate. In addition, the flow path 54 may be provided on a substrate, the pump head of the fluid machine 55 may be in contact with the flow path, and the drive unit of the fluid machine 55 may be removable from the substrate.

The flow paths 51, 54, and 56 may have a structure in which the inside can be closed from the outside air. The closed space including the inside of the flow paths 51, 54, and 56 may have a configuration in which gases, viruses, microorganisms, impurities and the like are not exchanged with the outside. The flow paths 51, 54, and 56 may be embedded and enclosed in a non-gas-permeable substance. At least a part of the flow paths 51, 54, and 56 may be provided on a member such as a plate. At least a part of the flow paths 51, 54, and 56 may be formed by carving into a member. At least a part of the flow paths 51, 54, and 56 may be carved into a member and formed by superimposing recesses.

In the case where the mixed solution containing the blood and the erythrocyte precipitating agent or the erythrocyte removal agent is transported to an erythrocyte remover 11, the fluid machine 52 moves the blood in the blood container 50 into the mixer 57 through the flow paths 51 and 56. In addition, the fluid machine 55 moves the erythrocyte precipitating agent or the erythrocyte removal agent in the erythrocyte treatment agent container 53 into the mixer 57 through the flow paths 54 and 56. Here, a fluid machine may not be provided in the flow paths 51 and 54, a fluid machine may be provided in the flow path 56, and the fluid machine provided in the flow path 56 may move the blood in the blood container 50 and the erythrocyte precipitating agent or the erythrocyte removal agent in the erythrocyte treatment agent container 53 into the mixer 57. In the mixer 57, the blood and the erythrocyte precipitating agent or the erythrocyte removal agent are mixed.

The erythrocyte removal device 100 further includes the erythrocyte remover 11 that at least partially removes erythrocytes from the blood. A flow path 58 for transporting the mixed solution containing the blood and the erythrocyte precipitating agent or the erythrocyte removal agent mixed in the mixer 57 into the erythrocyte remover 11 is connected to the mixer 57. The mixed solution containing the blood and the erythrocyte precipitating agent or the erythrocyte removal agent mixed in the mixer 57 is transported to the erythrocyte remover 11 through the flow path 58.

The flow path 58 may have a structure in which the inside can be closed from the outside air. The closed space including the inside of the flow path 58 may have a configuration in which gases, viruses, microorganisms, impurities and the like are not exchanged with the outside. The flow path 58 may be embedded and enclosed in a non-gas-permeable substance. At least a part of the flow path 58 may be provided on a member such as a plate. At least a part of the flow path 58 may be formed by carving into a member. At least a part of the flow path 58 may be carved into a member and formed by superimposing recesses.

The erythrocyte remover 11 may have a structure in which the inside can be closed from the outside air. The closed space including the inside of the erythrocyte remover 11 may have a configuration in which gases, viruses, microorganisms, impurities and the like are not exchanged with the outside. The erythrocyte remover 11 may be embedded and enclosed in a non-gas-permeable substance. At least a part of the erythrocyte remover 11 may be provided on a member such as a plate. At least a part of the erythrocyte remover 11 may be formed by carving into a member. At least a part of the erythrocyte remover 11 may be carved into a member and formed by superimposing recesses. The volume of the erythrocyte remover 11 can change its volume.

In the case where the blood is mixed with the erythrocyte precipitating agent in the mixer 57, erythrocytes are precipitated in the erythrocyte remover 11, and the erythrocytes are at least partially removed from the blood. In the case where the blood is mixed with the erythrocyte removal agent in the mixer 57, erythrocytes in the erythrocyte remover 11 are hemolyzed, and the erythrocytes are at least partially removed from the blood.

A storage tank 130 is connected to the erythrocyte remover 11, for example, through a flow path 131. The storage tank 130 and the flow path 131 may be connected by a connector. The flow path 131 may have a structure in which the inside can be closed from the outside air. The closed space including the inside of the flow path 131 may have a configuration in which gases, viruses, microorganisms, impurities and the like are not exchanged with the outside. The flow path 131 may be embedded and enclosed in a non-gas-permeable substance. At least a part of the flow path 131 may be provided on a member such as a plate. At least a part of the flow path 131 may be formed by carving into a member. At least a part of the flow path 131 may be carved into a member and formed by superimposing recesses. A fluid machine such as a pump for moving the fluid in the flow path 131 may be provided in the flow path 131.

The storage tank 130 may have a structure in which the inside can be closed from the outside air. The closed space including the inside of the storage tank 130 may have a configuration in which gases, viruses, microorganisms, impurities and the like are not exchanged with the outside. The storage tank 130 may be embedded and enclosed in a non-gas-permeable substance. At least a part of the storage tank 130 may be provided on a member such as a plate. At least a part of the storage tank 130 may be formed by carving into a member. At least a part of the storage tank 130 may be carved into a member and formed by superimposing recesses. The storage tank 130 can change its volume. In this case, for example, the storage tank 130 includes a syringe for storing a fluid and a plunger which is inserted into the syringe and movable in the syringe, and the volume for storing the fluid in the syringe can be changed by moving the plunger. Alternatively, the storage tank 130 may be a flexible bellows or bag.

In the case where the mixed solution containing the blood and the erythrocyte precipitating agent or the erythrocyte removal agent is transported into the erythrocyte remover 11 from the flow path 58, the fluid such as air in the erythrocyte remover 11 may move, for example, in the storage tank 130, and the storage tank 130 may expand its volume and receive the fluid that has moved from the inside of the erythrocyte remover 11. Here, the storage tank 130 may actively expand or passively expand its volume upon receiving pressure.

The erythrocyte removal device 100 may further include a mononuclear cell collector 15 which receives the treated blood from which the erythrocytes are at least partially removed from the erythrocyte remover 11 and collects mononuclear cells from the treated blood. The mononuclear cell collector 15 may have a structure in which the inside can be closed from the outside air. The closed space including the inside of the mononuclear cell collector 15 may have a configuration in which gases, viruses, microorganisms, impurities and the like are not exchanged with the outside. The mononuclear cell collector 15 may be embedded and enclosed in a non-gas-permeable substance. At least a part of the mononuclear cell collector 15 may be provided on a member such as a plate. At least a part of the mononuclear cell collector 15 may be formed by carving into a member. At least a part of the mononuclear cell collector 15 may be carved into a member and formed by superimposing recesses. The mononuclear cell collector 15 can change its volume.

Figure 3:
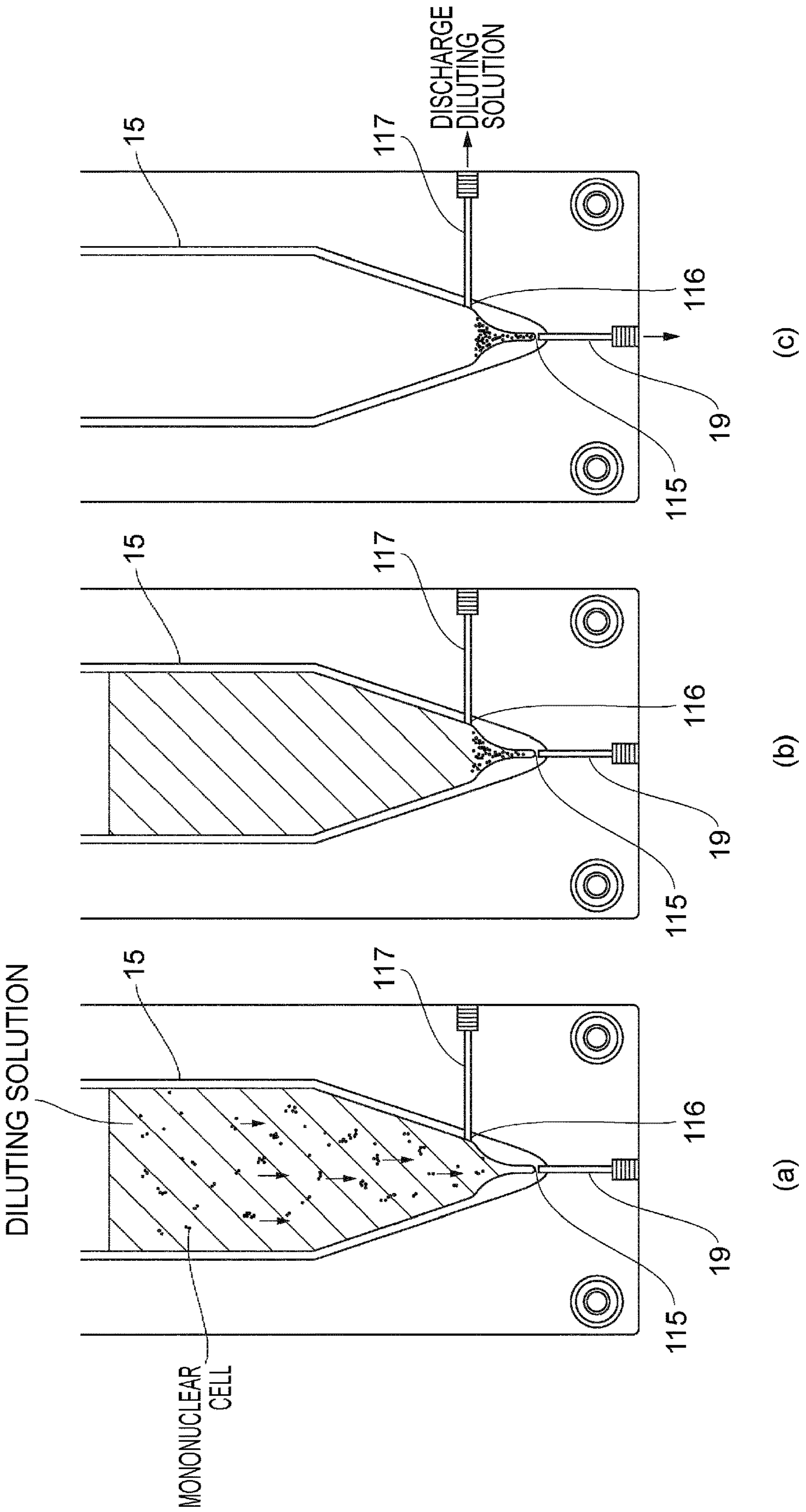
FIG. 3 is a schematic view of a mononuclear cell collector according to an embodiment.

As shown in FIG. 3, for example, a first opening 115 is provided at the bottom of the mononuclear cell collector 15, and a second opening 116 is provided at the side surface of the mononuclear cell collector 15. The position of the first opening 115 is below the second opening 116 in the direction of gravity.

A flow path 19 is connected to the first opening 115 of the mononuclear cell collector 15. The flow path 19 may have a structure in which the inside can be closed from the outside air. The closed space including the inside of the flow path 19 may have a configuration in which gases, viruses, microorganisms, impurities and the like are not exchanged with the outside. The flow path 19 may be embedded and enclosed in a non-gas-permeable substance. At least a part of the flow path 19 may be provided on a member such as a plate. At least a part of the flow path 19 may be formed by carving into a member. At least a part of the flow path 19 may be carved into a member and formed by superimposing recesses.

A flow path 117 is connected to the second opening 116 of the mononuclear cell collector 15. The flow path 117 may have a structure in which the inside can be closed from the outside air. The closed space including the inside of the flow path 117 may have a configuration in which gases, viruses, microorganisms, impurities and the like are not exchanged with the outside. The flow path 117 may be embedded and enclosed in a non-gas-permeable substance. At least a part of the flow path 117 may be formed by carving into a member. At least a part of the flow path 117 may be provided on a member such as a plate. At least a part of the flow path 117 may be carved into a member and formed by superimposing recesses. As shown in FIG. 1, a fluid machine 21 such as a pump for moving the fluid in the flow path 117 is provided in the flow path 117. A valve other than the fluid machine may not be provided in the flow path 117.

The fluid machine 21 may include a pump head and a drive unit that drives the pump head. The flow path 117 may be provided on a substrate, the pump head of the fluid machine 21 may be in contact with the flow path 117, and the drive unit of the fluid machine 21 may be removable from the substrate.

As shown in FIG. 3, the mononuclear cell collector 15 may have a funnel-like bottom. In this case, for example, the first opening 115 is provided at the tip of the funnel-like bottom of the mononuclear cell collector 15, and the second opening 116 is provided at the side surface of the funnel-like bottom. A filter through which mononuclear cells cannot pass may be provided at the second opening 116.

In the mononuclear cell collector 15, a diluting solution such as a buffer solution can be stored therein. As shown in FIG. 1, the diluting solution may be introduced into the mononuclear cell collector 15 through a flow path 60 from a dilution liquid container 61 in which a liquid for dilution is stored. The dilution liquid container 61 and the flow path 60 may be connected by a connector. A fluid machine 62 such as a pump for moving the fluid in the flow path 60 may be provided in the flow path 60. A valve other than the fluid machine may not be provided in the flow path 60. The dilution liquid container 61 can change its volume. In addition, for example, the insides of the flow path 19 and the flow path 117 are filled with the diluting solution.

The fluid machine 62 may include a pump head and a drive unit that drives the pump head. The flow path 60 may be provided on a substrate, the pump head of the fluid machine 62 may be in contact with the flow path 60, and the drive unit of the fluid machine 62 may be removable from the substrate.

At least one of the dilution liquid container 61 and the flow path 60 may have a structure in which the inside can be closed from the outside air. The closed space including the inside of the dilution liquid container 61 and the flow path 60 may have a configuration in which gases, viruses, microorganisms, impurities and the like are not exchanged with the outside. The dilution liquid container 61 and the flow path 60 may be embedded and enclosed in a non-gas-permeable substance. At least a part the dilution liquid container 61 and the flow path 60 may be provided on a member such as a plate. At least a part of the dilution liquid container 61 and the flow path 60 may be formed by carving into a member. At least a part of the dilution liquid container 61 and the flow path 60 may be carved into a member and formed by superimposing recesses.

As shown in FIG. 1, a flow path 17 for transporting the treated blood from which the erythrocytes are at least partially removed from the erythrocyte remover 11 to the mononuclear cell collector 15 is provided between the erythrocyte remover 11 and the mononuclear cell collector 15. A fluid machine 18 such as a pump for moving the fluid in the flow path 17 is provided in the flow path 17. A valve other than the fluid machine may not be provided in the flow path 17. The flow path 17 may have a structure in which the inside can be closed from the outside air. The closed space including the inside of the flow path 17 may have a configuration in which gases, viruses, microorganisms, impurities and the like are not exchanged with the outside. The flow path 17 may be embedded and enclosed in a non-gas-permeable substance. At least a part of the flow path 17 may be provided on a member such as a plate. At least a part of the flow path 17 may be formed by carving into a member. At least a part of the flow path 17 may be carved into a member and formed by superimposing recesses.

The fluid machine 18 aspirates the treated blood from which the erythrocytes are at least partially removed in the erythrocyte remover 11 through the flow path 17, and supplies the aspirated treated blood from which the erythrocytes are at least partially removed into the mononuclear cell collector 15. In the case where the erythrocytes are precipitated in the erythrocyte remover 11, the supernatant in the erythrocyte remover 11 is transported to the mononuclear cell collector 15 as the treated blood from which the erythrocytes are at least partially removed.

The fluid machine 18 may include a pump head and a drive unit that drives the pump head. The flow path 17 may be provided on a substrate, the pump head of the fluid machine 18 may be in contact with the flow path 17, and the drive unit of the fluid machine 18 may be removable from the substrate.

The treated blood from which the erythrocytes are at least partially removed, which has been transported to the mononuclear cell collector 15, is diluted with the diluting solution as shown in FIG. 3(*a*). In the diluted treated blood solution, platelets float, and mononuclear cells precipitate toward the bottom of the mononuclear cell collector 15. Here, the diluting solution may contain a erythrocyte removal agent. In this case, erythrocytes remaining in the treated blood solution are hemolyzed.

As shown in FIG. 3(*b*), the precipitated mononuclear cells accumulate at the tip of the funnel-like bottom of the mononuclear cell collector 15. After mononuclear cells precipitate in the diluted treated blood solution, as shown in FIG. 3(*c*), the fluid machine 21 (shown in FIG. 1) provided in the flow path 117 connected to the second opening 116 of the mononuclear cell collector 15 aspirates the diluted treated blood solution which is the supernatant. The aspiration power for aspirating the supernatant is set so that it is difficult to aspirate the precipitated mononuclear cells. The supernatant contains the platelets and the hemolyzed erythrocytes. Therefore, by removing the supernatant from the mononuclear cell collector 15 by aspiration, it is possible to separate the mononuclear cells from the platelets and the erythrocytes. The aspirated supernatant may be transported to the erythrocyte remover 11. In addition, the aspirated supernatant may be transported to the storage tank 130 through the erythrocyte remover 11 and the flow path 131. In addition, a gas having approximately the same volume as that of the supernatant aspirated from the mononuclear cell collector 15 may be transported from the erythrocyte remover 11 into the mononuclear cell collector 15. Alternatively, a diluting solution having approximately the same volume as that of the supernatant aspirated from the mononuclear cell collector 15 may be transported from the dilution liquid container 61 into the mononuclear cell collector 15.

After the mononuclear cells are precipitated, supply of a diluting solution into the mononuclear cell collector 15 and removal of the supernatant from the mononuclear cell collector 15 by aspiration may be repeated.

A mononuclear cell aspiration device 20 that aspirates the mononuclear cells accumulated at the bottom of the mononuclear cell collector 15 is provided in the flow path 19. A fluid machine such as a pump can be used as the mononuclear cell aspiration device 20. A valve other than the fluid machine may not be provided in the flow path 19. For example, the size of the first opening 115 shown in FIG. 3 is set so that, in the case where the mononuclear cell aspiration device 20 does not aspirate mononuclear cells, the mononuclear cells are clogged in the first opening 115, and in the case where the mononuclear cell aspiration device 20 aspirates mononuclear cells, the mononuclear cells can pass through the first opening 115. In the case where the mononuclear cell aspiration device 20 aspirates the mononuclear cells, the mononuclear cells move from the inside of the mononuclear cell collector 15 to the flow path 19.

The mononuclear cell aspiration device 20 may include a pump head and a drive unit that drives the pump head. The flow path 19 may be provided on a substrate, the pump head of the mononuclear cell aspiration device 20 may be in contact with the flow path 19, and the drive unit of the mononuclear cell aspiration device 20 may be removable from the substrate.

Here, in the case where the inside of the mononuclear cell collector 15 is pressurized, the mononuclear cells in the mononuclear cell collector 15 may be moved to the flow path 19. In this case, the mononuclear cell aspiration device 20 may or may not be provided in the flow path 19.

As shown in FIG. 1 and FIG. 2, the flow path 19 is connected to the cell culture vessel 22. The mononuclear cells are transported from the mononuclear cell collector 15 to the cell culture vessel 22 through the flow path 19. Here, the cell culture vessel 22 may not be connected to the mononuclear cell collector 15, and the cells put into the cell culture vessel 22 are not limited to mononuclear cells. The cells transported to the cell culture vessel 22 may be stem cells, fibroblasts, nerve cells, retinal epithelial cells, hepatocytes, β cells, renal cells, mesenchymal stem cells, blood cells, megakaryocytes, T cells, chondrocytes, cardiomyocytes, muscle cells, vascular cells, epithelial cells, pluripotent stem cells, ES cells, iPS cells, or other somatic cells. The cells transported to the cell culture vessel 22 are arbitrary.

Figure 4:
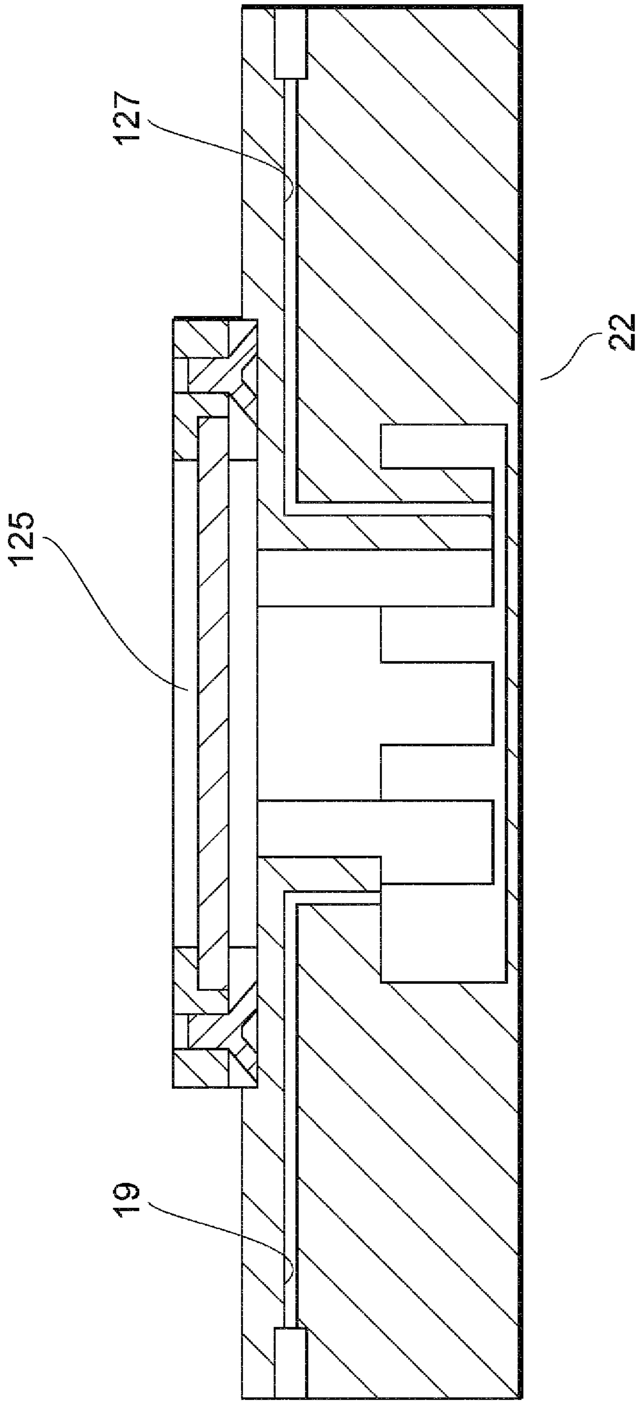
FIG. 4 is a schematic cross-sectional view of a cell culture vessel according to an embodiment.

As shown in FIG. 4, the cell culture vessel 22 may have a structure in which the inside can be closed from the outside air. The closed space including the inside of the cell culture vessel 22 may have a configuration in which gases, viruses, microorganisms, impurities and the like are not exchanged with the outside. The cell culture vessel 22 may be embedded and enclosed in a non-gas-permeable substance. At least a part of the cell culture vessel 22 may be provided on a member such as a plate. At least a part of the cell culture vessel 22 may be formed by carving into a member. At least a part of the cell culture vessel 22 may be carved into a member and formed by superimposing recesses. The shape of the cell culture vessel 22 is not particularly limited. The cell culture vessel 22 may have a horizontally long shape or vertically long shape with respect to the horizontal plane.

In the cell culture vessel 22, cells may be adhesive-cultured or cells may be suspended-cultured. In the case where the cells are adhesive-cultured, the inside of the cell culture vessel 22 may be coated with a cell adhesion coating agent such as Matrigel, collagen, polylysine, fibronectin, vitronectin, or laminin.

As shown in FIG. 1 and FIG. 2, a coating agent container 35 may be connected to the cell culture vessel 22, for example, through a flow path 34. The coating agent container 35 stores the cell adhesion coating agent. The coating agent container 35 may have a structure in which the inside can be closed from the outside air. The closed space including the inside of the coating agent container 35 may have a configuration in which gases, viruses, microorganisms, impurities and the like are not exchanged with the outside. The coating agent container 35 may be embedded and enclosed in a non-gas-permeable substance. At least a part of the coating agent container 35 may be provided on a member such as a plate. At least a part of the coating agent container 35 may be formed by carving into a member. At least a part of the coating agent container 35 may be carved into a member and formed by superimposing recesses. The coating agent container 35 can change its volume. In this case, for example, the coating agent container 35 includes a syringe for storing a fluid and a plunger which is inserted into the syringe and movable in the syringe, and the volume for storing the fluid in the syringe can be changed by moving the plunger. Alternatively, the coating agent container 35 may be a flexible bellows or bag.

The coating agent container 35 and the flow path 34 may be connected by a connector. The flow path 34 may have a structure in which the inside can be closed from the outside air. The closed space including the inside of the flow path 34 may have a configuration in which gases, viruses, microorganisms, impurities and the like are not exchanged with the outside. The flow path 34 may be embedded and enclosed in a non-gas-permeable substance. At least a part of the flow path 34 may be provided on a member such as a plate. At least a part of the flow path 34 may be formed by carving into a member. At least a part of the flow path 34 may be carved into a member and formed by superimposing recesses. A fluid machine 36 such as a pump for moving the fluid in the flow path 34 may be provided in the flow path 34. A valve other than the fluid machine may not be provided in the flow path 34.

The fluid machine 36 may include a pump head and a drive unit that drives the pump head. The flow path 34 may be provided on a substrate, the pump head of the fluid machine 36 may be in contact with the flow path 34, and the drive unit of the fluid machine 36 may be removable from the substrate.

In order to coat the inside of the cell culture vessel 22 with the cell adhesion coating agent, the fluid machine 36 moves the cell adhesion coating agent in the coating agent container 35 into the cell culture vessel 22 through the flow path 34. The fluid machine 36 may quantitatively move the cell adhesion coating agent in the coating agent container 35 into the cell culture vessel 22. In the case where the cell adhesion coating agent is supplied to the cell culture vessel 22, the coating agent container 35 may contract its volume.

The storage tank 130 is connected to the cell culture vessel 22, for example, through a flow path 132 or a flow path 134. The flow paths 132 and 134 may have a structure in which the inside can be closed from the outside air. The closed space including the inside of the flow paths 132 and 134 may have a configuration in which gases, viruses, microorganisms, impurities and the like are not exchanged with the outside. The flow paths 132 and 134 may be embedded and enclosed in a non-gas-permeable substance.

At least a part of the flow paths 132 and 134 may be provided on a member such as a plate. At least a part of the flow paths 132 and 134 may be formed by carving into a member. At least a part of the flow paths 132 and 134 may be carved into a member and formed by superimposing recesses. A fluid machine 133 such as a pump for moving the fluid in the flow path 132 may be provided in the flow path 132. A valve other than the fluid machine may not be provided in the flow path 132. The same applies to the flow path 134.

The fluid machine 133 may include a pump head and a drive unit that drives the pump head. The flow path 132 may be provided on a substrate, the pump head of the fluid machine 133 may be in contact with the flow path 132, and the drive unit of the fluid machine 133 may be removable from the substrate.

In the case where the cell adhesion coating agent is transported from the flow path 34 into the cell culture vessel 22, the fluid such as a gas, for example, air, in the cell culture vessel 22 may move, for example, into the storage tank 130, and the storage tank 130 may expand its volume and receive the fluid that has moved from the inside of the cell culture vessel 22.

The inside of the cell culture vessel 22 may be separated by a medium component permeable member through which cells cannot permeate but medium components and waste product can permeate. In the case where cells are suspended-cultured, the inner wall of the cell culture vessel 22 may be coated with a non-cell-adhesive substance such as poly2-hydroxyethylmethacrylate (poly-HEMA) so that cells do not adhere, and the inner wall of the cell culture vessel 22 may be non-adhesive to cells. As shown in FIG. 4, a window through which the inside can be observed may be provided in the cell culture vessel 22. As the material of the window, for example, glass or a resin can be used.

A temperature adjuster for heating and cooling a window may be provided in the cell culture vessel 22. The temperature adjuster may be a transparent heater such as a transparent conductive film that is disposed on the window and heats the window. Alternatively, the cell culture vessel 22 may include a temperature adjuster for heating and cooling a housing. In the case where the temperature of the housing is adjusted by the temperature adjuster, it is possible to adjust the temperature of the medium in the cell culture vessel 22. The cell culture vessel 22 may further include a thermometer that measures the temperature of the medium in the cell culture vessel 22. The thermometer may measure the temperature of the medium based on the temperature of the cell culture vessel 22 without coming into contact with the medium or may come into contact with the medium and directly measure the temperature of the medium. In this case, the temperature adjuster may be feedback-controlled so that the temperature of the medium becomes a predetermined temperature. The temperature of the medium is adjusted, for example, from 20° C. to 45° C.

Figure 5:
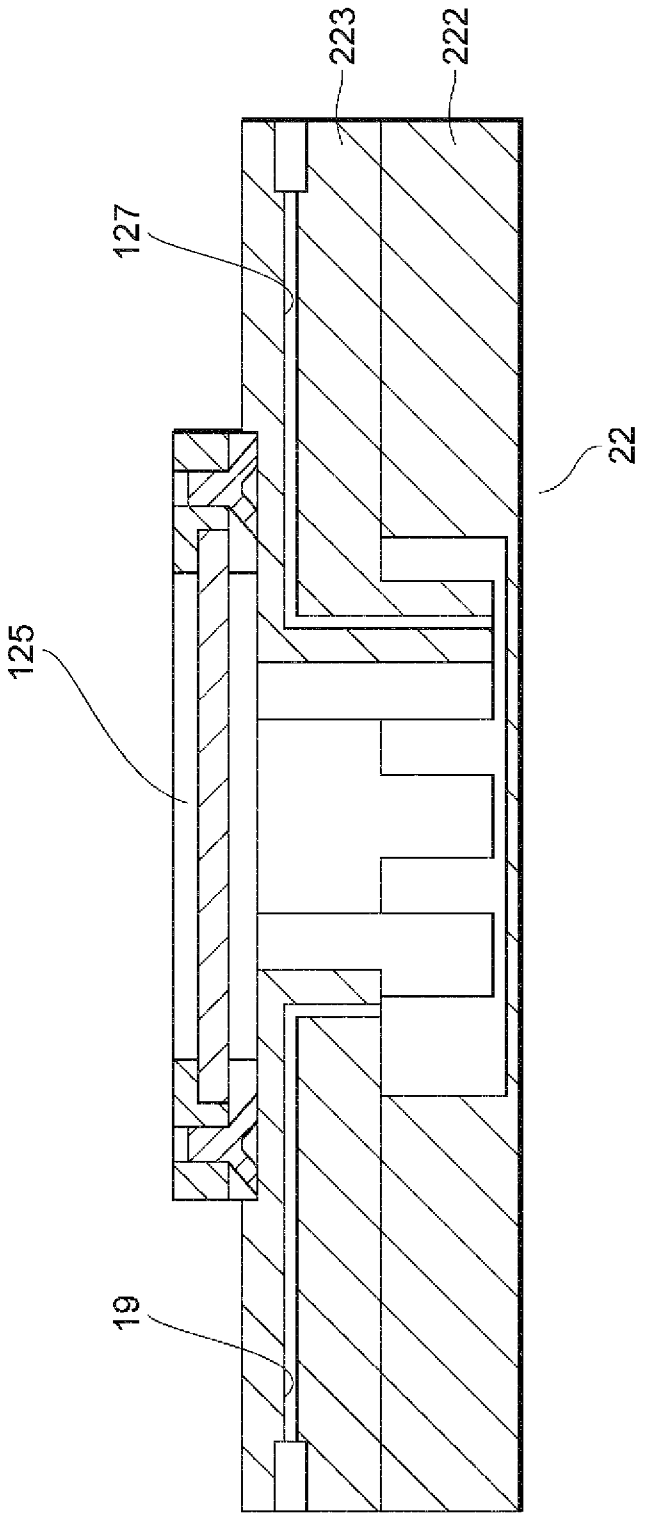
FIG. 5 is a schematic cross-sectional view of a cell culture vessel according to an embodiment.

The cell culture vessel 22 may be integrally molded. The cell culture vessel 22 may be produced by a 3D printer method. Examples of 3D printer methods include a material extrusion deposition method, a material jetting method, a binder jetting method and an optically shaping method. Alternatively, as shown in FIG. 5, the cell culture vessel 22 may include a first housing 222 having a bottom surface and a second housing 223 which is disposed on the first housing 222 and has a top surface that faces the bottom surface, and the first housing 222 and the second housing 223 may be combined to form the interior. The flow path connected to the cell culture vessel 22 may be provided in at least one of the first housing 222 and the second housing 223. A petri dish or the like can be disposed as an internal culture container inside the cell culture vessel 22. In this case, the flow path is configured to supply a fluid into the internal culture container.

As shown in FIG. 1 and FIG. 2, a flow path 23 is connected to the flow path 19 connected to the cell culture vessel 22. The flow path 23 may have a structure in which the inside can be closed from the outside air. The closed space including the inside of the flow path 23 may have a configuration in which gases, viruses, microorganisms, impurities and the like are not exchanged with the outside. The flow path 23 may be embedded and enclosed in a non-gas-permeable substance. At least a part of the flow path 23 may be provided on a member such as a plate. At least a part of the flow path 23 may be formed by carving into a member. At least a part of the flow path 23 may be carved into a member and formed by superimposing recesses. A fluid machine 24 such as a pump for moving the fluid in the flow path 23 is provided in the flow path 23. A valve other than the fluid machine may not be provided in the flow path 23.

The fluid machine 24 may include a pump head and a drive unit that drives the pump head. The flow path 23 may be provided on a substrate, the pump head of the fluid machine 24 may be in contact with the flow path 23, and the drive unit of the fluid machine 24 may be removable from the substrate.

For example, a medium container 25, which is a fluid container for storing a medium suitable for cells before a factor is introduced, is connected to the flow path 23. The medium container 25 and the flow path 23 may be connected by a connector. For example, in the case where the cells before a factor is introduced are somatic cells such as differentiated cells, the medium stored in the medium container 25 is a somatic cell medium. For example, in the case where the cells before a factor is introduced are mononuclear cells, the medium stored in the medium container 25 is a blood cell medium. For example, in the case where the cells before a factor is introduced are stem cells, the medium stored in the medium container 25 is a stem cell medium. The stem cells may be iPS cells, embryonic stem cells (ES cells), somatic stem cells or other artificially induced stem cells. Examples of stem cell mediums include an induction culture medium, an expansion culture medium and a maintenance culture medium. The medium stored in the medium container 25 may be a gel or a liquid. Cells may be adhesive-cultured (2D cultured) in a gel medium or a liquid medium, and cells may be suspended-cultured (3D cultured) in a gel medium or a liquid medium.

In the case where the medium is gel-like, the medium may contain a polymer compound. For example, the polymer compound may be at least one selected from the group consisting of gellan gum, deacylated gellan gum, hyaluronic acid, rhamsan gum, diutan gum, xanthan gum, carrageenan, fucoidan, pectin, pectic acid, pectinic acid, heparan sulfate, heparin, heparitin sulfate, keratosulfate, chondroitin sulfate, dermatan sulfate, rhamnan sulfate, and salts thereof. In addition, the medium may contain methyl cellulose. In the case where the medium contains methyl cellulose, aggregation between cells is further reduced.

Alternatively, the medium may contain a small amount of a temperature-sensitive gel selected from among poly(glycerol monomethacrylate) (PGMA), poly(2-hydroxypropylmethacrylate) (PHPMA), poly(N-isopropylacrylamide) (PNIPAM), amine terminated, carboxylic acid terminated, maleimide terminated, N-hydroxysuccinimide (NHS) ester terminated, triethoxysilane terminated, poly(N-isopropylacrylamide-co-acrylamide), poly(N-isopropylacrylamide-co-acrylic acid), poly(N-isopropylacrylamide-co-butylacrylate), poly(N-isopropylacrylamide-co-methacrylic acid), poly(N-isopropylacrylamide-co-methacrylic acid-co-octadecylacrylate), and N-isopropylacrylamide.

Here, in the present disclosure, the gel-like medium or gel medium includes a polymer medium.

The medium container 25 may have a structure in which the inside can be closed from the outside air. The closed space including the inside of the medium container 25 may have a configuration in which gases, viruses, microorganisms, impurities and the like are not exchanged with the outside. The medium container 25 may be embedded and enclosed in a non-gas-permeable substance. At least a part of the medium container 25 may be provided on a member such as a plate. At least a part of the medium container 25 may be formed by carving into a member. At least a part of the medium container 25 may be carved into a member and formed by superimposing recesses. The volume of the medium container 25 can change its volume. In this case, for example, the medium container 25 includes a syringe for storing a somatic cell medium and a plunger which is inserted into the syringe and movable in the syringe, and the volume for storing the somatic cell medium in the syringe can be changed by moving the plunger. Alternatively, the medium container 25 may be a flexible bellows or bag.

In the case where mononuclear cells are transported from the mononuclear cell collector 15 to the flow path 19, the fluid machine 24 transports the medium from the medium container 25 to the flow path 19 through the flow path 23. The medium container 25 reduces the volume at which the medium can be stored. Here, the medium container 25 may actively contract its volume or may passively contract its volume with aspiration power from the inside of the flow path 23. The somatic cell medium transported to the flow path 19 through the flow path 23 is mixed with the mononuclear cells in the flow path 19 and transported into the cell culture vessel 22.

A temperature adjusting device configured to adjust the temperature of the medium in the medium container 25 may be provided at the medium container 25.

In the case where cells and a medium are transported from the flow path 19 into the cell culture vessel 22, the excess fluid in the cell culture vessel 22 may move, for example, into the storage tank 130, and the storage tank 130 may expand its volume and receive the fluid that has moved from the inside of the cell culture vessel 22.

The factor container 81 for storing the factor and the reagent container 82 for storing the reagent for introducing the factor into cells are connected to the cell culture vessel 22 through a flow path.

The factor container 81 stores the factor to be introduced into cells therein. The factor may be referred to as a payload with respect to a reagent that introduces a factor into cells. The factor may be a nucleic acid such as DNA, RNA, and an oligonucleotide, and may be a protein, a compound, or a virus. The DNA may be plasmid DNA. The RNA may be mRNA, siRNA, or miRNA. The RNA may be modified RNA or unmodified RNA. The protein may be a nuclease protein such as Cas9 protein. The virus may be a lentivirus. The factor may be an inducing factor that induces cells in a first state into cells in a second state.

In the present disclosure, induction refers to reprogramming, initialization, transformation, transdifferentiation (transdifferentiation or lineage reprogramming), differentiation induction, cell fate change (cell fate reprogramming) or the like. A factor that induces cells other than pluripotent stem cells into pluripotent stem cells is called a reprogramming factor. Examples of reprogramming factors include OCT3/4, SOX2, KLF4, and c-MYC. A factor that induces stem cells into differentiated cells is called a differentiation-inducing factor. Examples of differentiated cells include fibroblasts, nerve cells, retinal epithelial cells, hepatocytes, β cells, renal cells, mesenchymal stem cells, blood cells, megakaryocytes, T cells, chondrocytes, cardiomyocytes, muscle cells, vascular cells, epithelial cells, pluripotent stem cells, ES cells, iPS cells, or other somatic cells.

The factor container 81 may have a structure in which the inside can be closed from the outside air. The closed space including the inside of the factor container 81 may have a configuration in which gases, viruses, microorganisms, impurities and the like are not exchanged with the outside. The factor container 81 may be embedded and enclosed in a non-gas-permeable substance. At least a part of the factor container 81 may be provided on a member such as a plate. At least a part of the factor container 81 may be formed by carving into a member. At least a part of the factor container 81 may be carved into a member and formed by superimposing recesses. The factor container 81 can change its volume. In this case, for example, the factor container 81 includes a syringe for storing a fluid and a plunger which is inserted into the syringe and movable in the syringe, and the volume for storing the fluid in the syringe can be changed by moving the plunger. Alternatively, the factor container 81 may be a flexible bellows or bag.

The reagent container 82 stores the reagent for introducing the factor stored in the factor container 81 into cells. Examples of reagents include artificial liposomes, cationic lipids, calcium chloride, cationic diethylaminoethyldextran molecules, cationic peptides and derivatives thereof, linear or branched synthetic polymers, polysaccharide-based introduction molecules, natural polymers, and active and inactive dendrimers. The reagent is, for example, a transfection reagent. In the present disclosure, introduction of not only nucleic acids but also proteins, compounds, and viruses into cells is also referred to as transfection.

The reagent container 82 may have a structure in which the inside can be closed from the outside air. The closed space including the inside of the reagent container 82 may have a configuration in which gases, viruses, microorganisms, impurities and the like are not exchanged with the outside. The reagent container 82 may be embedded and enclosed in a non-gas-permeable substance. At least a part of the reagent container 82 may be provided on a member such as a plate. At least a part of the reagent container 82 may be formed by carving into a member. At least a part of the reagent container 82 may be carved into a member and formed by superimposing recesses. The reagent container 82 can change its volume. In this case, for example, the reagent container 82 includes a syringe for storing a fluid and a plunger which is inserted into the syringe and movable in the syringe, and the volume for storing the fluid in the syringe can be changed by moving the plunger. Alternatively, the reagent container 82 may be a flexible bellows or bag.

The cell culture device 200 further includes a diluting solution container 83 for storing a diluting solution for diluting each of the factor and the reagent. Examples of diluting solutions include phosphate buffered saline (PBS).

The diluting solution container 83 may have a structure in which the inside can be closed from the outside air. The closed space including the inside of the diluting solution container 83 may have a configuration in which gases, viruses, microorganisms, impurities and the like are not exchanged with the outside. The diluting solution container 83 may be embedded and enclosed in a non-gas-permeable substance. At least a part of the diluting solution container 83 may be provided on a member such as a plate. At least a part of the diluting solution container 83 may be formed by carving into a member. At least a part of the diluting solution container 83 may be carved into a member and formed by superimposing recesses. The diluting solution container 83 can change its volume. In this case, for example, the diluting solution container 83 includes a syringe for storing a fluid and a plunger which is inserted into the syringe and movable in the syringe, and the volume for storing the fluid in the syringe can be changed by moving the plunger. Alternatively, the diluting solution container 83 may be a flexible bellows or bag.

The cell culture device 200 further includes a factor diluting container 84 for mixing the factor and the diluting solution provided in a flow path between the factor container 81 and the diluting solution container 83, and the cell culture vessel 22. In the factor diluting container 84, the factor transported from the factor container 81 and the diluting solution transported from the diluting solution container 83 are mixed to prepare a factor diluting solution. The factor diluting container 84 may be a mixer including a bent flow path through which the factor diluting solution flows. The bent flow path may be bent in a spiral shape. The flow path may meander in the bent flow path. The cross-sectional area may repeatedly increase and decrease in size in the bent flow path.

The factor diluting container 84 may have a structure in which the inside can be closed from the outside air. The closed space including the inside of the factor diluting container 84 may have a configuration in which gases, viruses, microorganisms, impurities and the like are not exchanged with the outside. The factor diluting container 84 may be embedded and enclosed in a non-gas-permeable substance. At least a part of the factor diluting container 84 may be provided on a member such as a plate. At least a part of the factor diluting container 84 may be formed by carving into a member. At least a part of the factor diluting container 84 may be carved into a member and formed by superimposing recesses. The factor diluting container 84 can change its volume. In this case, for example, the factor diluting container 84 includes a syringe for storing a fluid and a plunger which is inserted into the syringe and movable in the syringe, and the volume for storing the fluid in the syringe can be changed by moving the plunger. Alternatively, the factor diluting container 84 may be a flexible bellows or bag.

A flow path 85 for transporting at least the factor from the factor container 81 to the factor diluting container 84 is connected to the factor container 81. The factor container 81 and the flow path 85 may be connected by a connector. A flow path 86 for transporting at least the diluting solution from the diluting solution container 83 to the factor diluting container 84 is connected to the diluting solution container 83. The diluting solution container 83 and the flow path 86 may be connected by a connector. The flow path 85 and the flow path 86 merge with a flow path 87. The flow path 87 is connected to the factor diluting container 84. A fluid machine 187 for moving the fluid in the flow path 85 may be provided in the flow path 85. A valve other than the fluid machine may not be provided in the flow path 85. A fluid machine 88 for moving the fluid in the flow path 86 may be provided in the flow path 86. A valve other than the fluid machine may not be provided in the flow path 86.

The fluid machines 88 and 187 may include a pump head and a drive unit that drives the pump head. The flow path 85 may be provided on a substrate, the pump head of the fluid machine 187 may be in contact with the flow path 85, and the drive unit of the fluid machine 187 may be removable from the substrate. In addition, the flow path 86 may be provided on a substrate, the pump head of the fluid machine 88 may be in contact with the flow path 86, and the drive unit of the fluid machine 88 may be removable from the substrate.

The flow paths 85, 86, and 87 may have a structure in which the inside can be closed from the outside air. The closed space including the inside of the flow paths 85, 86, and 87 may have a configuration in which gases, viruses, microorganisms, impurities and the like are not exchanged with the outside. The flow paths 85, 86, and 87 may be embedded and enclosed in a non-gas-permeable substance. At least a part of the flow paths 85, 86, and 87 may be provided on a member such as a plate. At least a part of the flow paths 85, 86, and 87 may be formed by carving into a member. At least a part of the flow paths 85, 86, and 87 may be carved into a member and formed by superimposing recesses.

The fluid machine 187 moves the factor in the factor container 81 into the factor diluting container 84 through the flow paths 85 and 87. In addition, the fluid machine 88 moves the diluting solution in the diluting solution container 83 into the factor diluting container 84 through the flow paths 86 and 87. The fluid machine 187 may quantitatively move the factor in the factor container 81 into the factor diluting container 84. The fluid machine 88 may quantitatively move the diluting solution in the diluting solution container 83 into the factor diluting container 84. Here, a fluid machine may not be provided in the flow paths 85 and 86, a fluid machine may be provided in the flow path 87, and the fluid machine provided in the flow path 87 may move the factor in the factor container 81 and the diluting solution in the diluting solution container 83 into the factor diluting container 84.

In the case where the factor is transported, the factor container 81 may contract its volume. The factor container 81 may actively contract its volume or may passively contract its volume with aspiration power from the flow path 85. In the case where the diluting solution is transported, the diluting solution container 83 may contract its volume. The diluting solution container 83 may actively contract its volume or may passively contract its volume with aspiration power from the flow path 86. In the case where the factor and the diluting solution are supplied, the factor diluting container 84 may expand its volume. The factor diluting container 84 may actively expand its volume, and may passively expand its volume according to the pressure from the flow path 87.

The factor diluting container 84 is connected to the storage tank 130 through, for example, flow paths 135, 136, and 137 and the flow path 131. The flow paths 135, 136, and 137 may have a structure in which the inside can be closed from the outside air. The closed space including the inside of the flow paths 135, 136, and 137 may have a configuration in which gases, viruses, microorganisms, impurities and the like are not exchanged with the outside. The flow paths 135, 136, and 137 may be embedded and enclosed in a non-gas-permeable substance. At least a part of the flow paths 135, 136, and 137 may be provided on a member such as a plate. At least a part of the flow paths 135, 136, and 137 may be formed by carving into a member. At least a part of the flow paths 135, 136, and 137 may be carved into a member and formed by superimposing recesses.

In the case where the factor and the diluting solution are transported to the factor diluting container 84, the fluid such as a gas, for example, air, in the factor diluting container 84 may move, for example, into the storage tank 130, and the storage tank 130 may expand its volume and receive the fluid that has moved from the inside of the factor diluting container 84.

The cell culture device 200 further includes a reagent diluting container 89 for mixing the reagent and the diluting solution provided in a flow path between the reagent container 82 and the diluting solution container 83, and the cell culture vessel 22. In the reagent diluting container 89, the reagent transported from the reagent container 82 and the diluting solution transported from the diluting solution container 83 are mixed to prepare a reagent diluting solution. The reagent diluting container 89 may be a mixer including a bent flow path through which the reagent diluting solution flows. The bent flow path may be bent in a spiral shape. The flow path may meander in the bent flow path. The cross-sectional area may repeatedly increase and decrease in size in the bent flow path.

The reagent diluting container 89 may have a structure in which the inside can be closed from the outside air. The closed space including the inside of the reagent diluting container 89 may have a configuration in which gases, viruses, microorganisms, impurities and the like are not exchanged with the outside. The reagent diluting container 89 may be embedded and enclosed in a non-gas-permeable substance. At least a part of the reagent diluting container 89 may be provided on a member such as a plate. At least a part of the reagent diluting container 89 may be formed by carving into a member. At least a part of the reagent diluting container 89 may be carved into a member and formed by superimposing recesses. The reagent diluting container 89 can change its volume. In this case, for example, the reagent diluting container 89 includes a syringe for storing a fluid and a plunger which is inserted into the syringe and movable in the syringe, and the volume for storing the fluid in the syringe can be changed by moving the plunger. Alternatively, the reagent diluting container 89 may be a flexible bellows or bag.

A flow path 90 for transporting at least the reagent from the reagent container 82 into the reagent diluting container 89 is connected to the reagent container 82. The reagent container 82 and the flow path 90 may be connected by a connector. A flow path 91 for transporting at least the diluting solution from the diluting solution container 83 into the reagent diluting container 89 is connected to the diluting solution container 83. The diluting solution container 83 and the flow path 91 may be connected by a connector. The flow path 90 and the flow path 91 merge with a flow path 92. The flow path 92 is connected to the reagent diluting container 89. A fluid machine 93 for moving the fluid in the flow path 90 may be provided in the flow path 90. A valve other than the fluid machine may not be provided in the flow path 90. A fluid machine 94 for moving the fluid in the flow path 91 may be provided in the flow path 91. A valve other than the fluid machine may not be provided in the flow path 91.

The fluid machines 93 and 94 may include a pump head and a drive unit that drives the pump head. The flow path 90 may be provided on a substrate, the pump head of the fluid machine 93 may be in contact with the flow path 90, and the drive unit of the fluid machine 93 may be removable from the substrate. In addition, the flow path 91 may be provided on a substrate, the pump head of the fluid machine 94 may be in contact with the flow path 91, and the drive unit of the fluid machine 94 may be removable from the substrate.

The flow paths 90, 91, and 92 may have a structure in which the inside can be closed from the outside air. The closed space including the inside of the flow paths 90, 91, and 92 may have a configuration in which gases, viruses, microorganisms, impurities and the like are not exchanged with the outside. The flow paths 90, 91, and 92 may be embedded and enclosed in a non-gas-permeable substance. At least a part of the flow paths 90, 91, and 92 may be provided on a member such as a plate. At least a part of the flow paths 90, 91, and 92 may be formed by carving into a member. At least a part of the flow paths 90, 91, and 92 may be carved into a member and formed by superimposing recesses.

The fluid machine 93 moves the reagent in the reagent container 82 into the reagent diluting container 89 through the flow paths 90 and 92. In addition, the fluid machine 94 moves the diluting solution in the diluting solution container 83 into the reagent diluting container 89 through the flow paths 91 and 92. The fluid machine 93 may quantitatively move the reagent in the reagent container 82 into the reagent diluting container 89. The fluid machine 94 may quantitatively move the diluting solution in the diluting solution container 83 into the reagent diluting container 89. Here, a fluid machine may not be provided in the flow paths 90 and 91, a fluid machine may be provided in the flow path 92, and the fluid machine provided in the flow path 92 may move the reagent in the reagent container 82 and the diluting solution in the diluting solution container 83 into the reagent diluting container 89.

In the case where the reagent is transported, the reagent container 82 may contract its volume. The reagent container 82 may actively contract its volume or may passively contract its volume with aspiration power from the flow path 90. In the case where the diluting solution is transported, the diluting solution container 83 may contract its volume. The diluting solution container 83 may actively contract its volume or may passively contract its volume with aspiration power from the flow path 91. In the case where the reagent and the diluting solution are supplied, the reagent diluting container 89 may expand its volume. The reagent diluting container 89 may actively expand its volume, and may passively expand its volume according to the pressure from the flow path 92.

The reagent diluting container 89 is connected to the storage tank 130 through, for example, the flow paths 135, 136, and 137, and the flow path 131. In the case where the reagent and the diluting solution are transported to the reagent diluting container 89, the fluid such as a gas, for example, air, in the reagent diluting container 89 may move, for example, into the storage tank 130, and the storage tank 130 may expand its volume and receive the fluid that has moved from the inside of the reagent diluting container 89.

The cell culture device 200 further includes a mixing tank 95 for mixing the factor and the reagent provided in a flow path between the factor diluting container 84 and the reagent diluting container 89, and the cell culture vessel 22. In the mixing tank 95, the factor diluting solution transported from the factor diluting container 84 and the reagent diluting solution transported from the reagent diluting container 89 are mixed to prepare a factor and reagent mixed solution. The mixing tank 95 may be a mixer including a bent flow path through which the factor and reagent mixed solution flows. The bent flow path may be bent in a spiral shape. The flow path may meander in the bent flow path. The cross-sectional area may repeatedly increase and decrease in size in the bent flow path.

The mixing tank 95 may have a structure in which the inside can be closed from the outside air. The closed space including the inside of the mixing tank 95 may have a configuration in which gases, viruses, microorganisms, impurities and the like are not exchanged with the outside. The mixing tank 95 may be embedded and enclosed in a non-gas-permeable substance. At least a part of the mixing tank 95 may be provided on a member such as a plate. At least a part of the mixing tank 95 may be formed by carving into a member. At least a part of the mixing tank 95 may be carved into a member and formed by superimposing recesses. The mixing tank 95 can change its volume. In this case, for example, the mixing tank 95 includes a syringe for storing a fluid and a plunger which is inserted into the syringe and movable in the syringe, and the volume for storing the fluid in the syringe can be changed by moving the plunger. Alternatively, the mixing tank 95 may be a flexible bellows or bag.

A flow path 96 for transporting at least the factor diluting solution from the factor diluting container 84 to the mixing tank 95 is connected to the factor diluting container 84. A flow path 97 for transporting at least the reagent diluting solution from the reagent diluting container 89 to the mixing tank 95 is connected to the reagent diluting container 89. The flow path 96 and the flow path 97 merge with a flow path 98. The flow path 98 is connected to the mixing tank 95. A fluid machine 99 for moving the fluid in the flow path 98 may be provided in the flow path 98. A valve other than the fluid machine may not be provided in the flow path 98.

The fluid machine 99 may include a pump head and a drive unit that drives the pump head. The flow path 98 may be provided on a substrate, the pump head of the fluid machine 99 may be in contact with the flow path 98, and the drive unit of the fluid machine 99 may be removable from the substrate.

The flow paths 96, 97, and 98 may have a structure in which the inside can be closed from the outside air. The closed space including the inside of the flow paths 96, 97, and 98 may have a configuration in which gases, viruses, microorganisms, impurities and the like are not exchanged with the outside. The flow paths 96, 97, and 98 may be embedded and enclosed in a non-gas-permeable substance. At least a part of the flow paths 96, 97, and 98 may be provided on a member such as a plate. At least a part of the flow paths 96, 97, and 98 may be formed by carving into a member. At least a part of the flow paths 96, 97, and 98 may be carved into a member and formed by superimposing recesses.

The fluid machine 99 moves the factor diluting solution in the factor diluting container 84 into the mixing tank 95 through the flow paths 96 and 98. In addition, the fluid machine 99 moves the reagent diluting solution in the reagent diluting container 89 into the mixing tank 95 through the flow paths 97 and 98. The fluid machine 99 may quantitatively move the factor diluting solution in the factor diluting container 84 into the mixing tank 95. The fluid machine 99 may quantitatively move the reagent diluting solution in the reagent diluting container 89 into the mixing tank 95. In the case where the factor diluting solution is transported, the factor diluting container 84 may contract its volume. The factor diluting container 84 may actively contract its volume or may passively contract its volume with aspiration power from the flow path 96. In the case where the reagent diluting solution is transported, the reagent diluting container 89 may contract its volume. The reagent diluting container 89 may actively contract its volume or may passively contract its volume with aspiration power from the flow path 97. In the case where the factor and the reagent are supplied, the mixing tank 95 may expand its volume. The mixing tank 95 may actively expand its volume, and may passively expand its volume according to the pressure from the flow path 98.

The mixing tank 95 is connected to the storage tank 130 through, for example, a flow path 137 and the flow path 131. In the case where the factor diluting solution and the reagent diluting solution are transported to the mixing tank 95, the fluid such as a gas, for example, air, in the mixing tank 95 may move, for example, in the storage tank 130, and the storage tank 130 may expand its volume and receive the fluid that has moved from the inside of the mixing tank 95.

Figure 8:
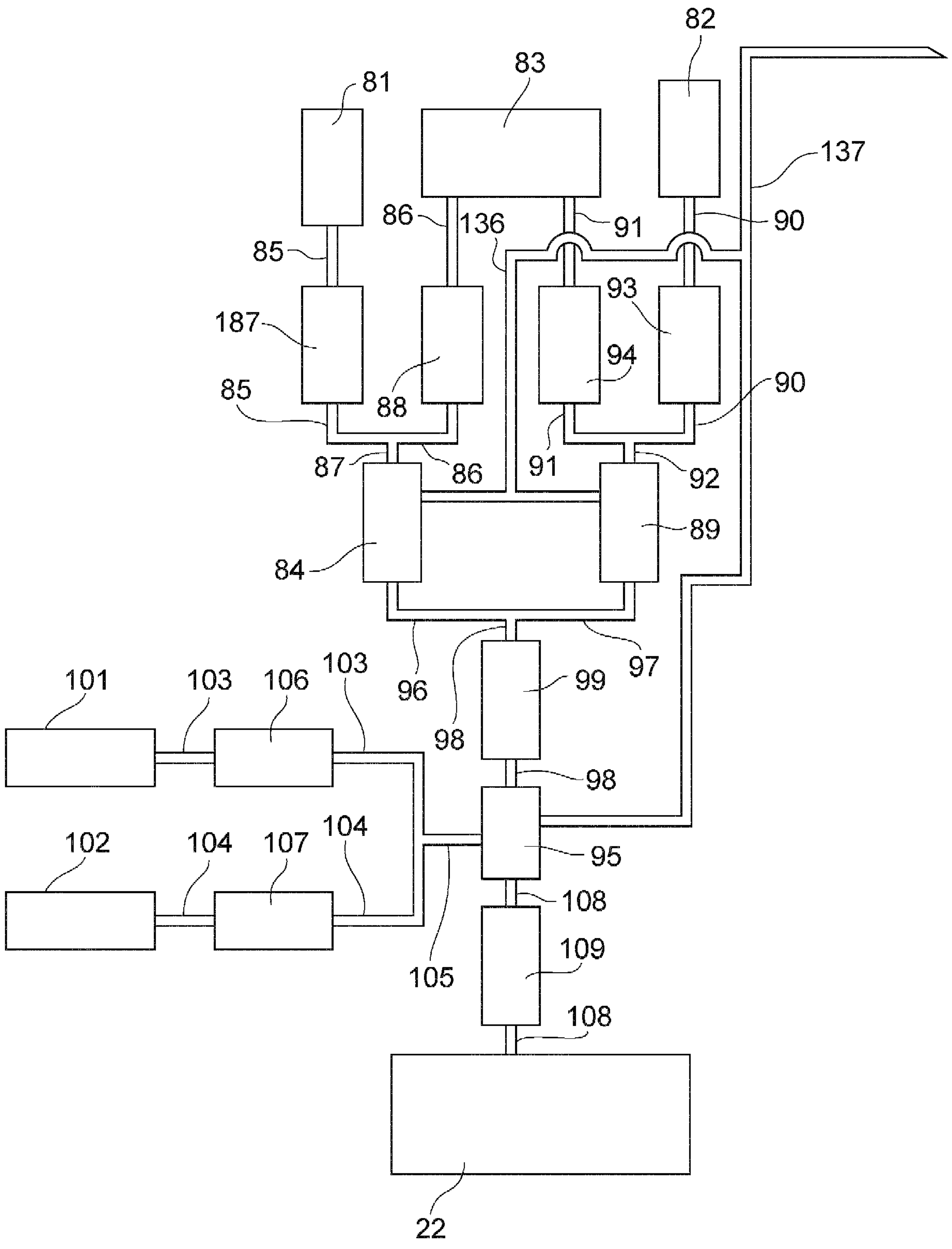
FIG. 8 is a schematic front view of a cell culture system according to an embodiment.
Figure 9:
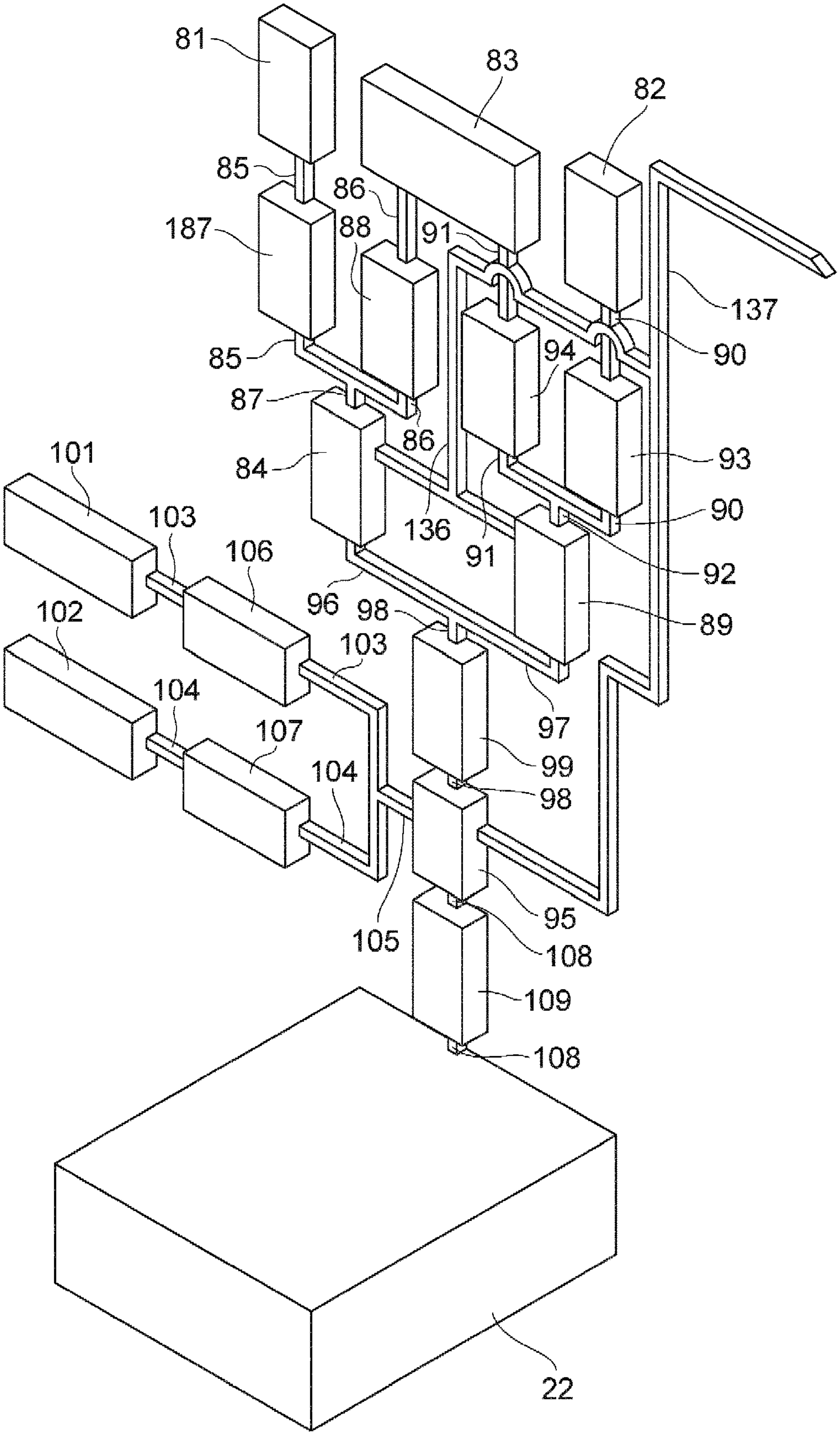
FIG. 9 is a schematic perspective view of a cell culture system according to an embodiment.

As shown in FIG. 8 and FIG. 9, a plurality of medium containers 101 and 102 for storing the medium to be supplied to the mixing tank 95 may be connected to the mixing tank 95.

The medium containers 101 and 102 may have a structure in which the inside can be closed from the outside air. The closed space including the inside of the medium containers 101 and 102 may have a configuration in which gases, viruses, microorganisms, impurities and the like are not exchanged with the outside. The medium containers 101 and 102 may be embedded and enclosed in a non-gas-permeable substance. At least a part of the medium containers 101 and 102 may be provided on a member such as a plate. At least a part of the medium containers 101 and 102 may be formed by carving into a member. At least a part of the medium containers 101 and 102 may be carved into a member and formed by superimposing recesses. The medium container 101 can change its volume. In this case, for example, the medium container 101 includes a syringe for storing a fluid and a plunger which is inserted into the syringe and movable in the syringe, and the volume for storing the fluid in the syringe can be changed by moving the plunger. Alternatively, the medium container 101 may be a flexible bellows or bag. The same applies to the medium container 101.

A flow path 103 for transporting at least the medium from the medium container 101 to the mixing tank 95 is connected to the medium container 101. The medium container 101 and the flow path 103 may be connected by a connector. A flow path 104 for transporting at least the medium from the medium container 102 to the mixing tank 95 is connected to the medium container 102. The medium container 102 and the flow path 104 may be connected by a connector. The flow path 103 and the flow path 104 merge with a flow path 105. The flow path 105 is connected to the mixing tank 95. A fluid machine 106 for moving the fluid in the flow path 103 may be provided in the flow path 103. A valve other than the fluid machine may not be provided in the flow path 103. A fluid machine 107 for moving the fluid in the flow path 104 may be provided in the flow path 104. A valve other than the fluid machine may not be provided in the flow path 104.

The fluid machines 106 and 107 may include a pump head and a drive unit that drives the pump head. The flow path 103 may be provided on a substrate, the pump head of the fluid machine 106 may be in contact with the flow path 103, and the drive unit of the fluid machine 106 may be removable from the substrate. In addition, the flow path 104 may be provided on a substrate, the pump head of the fluid machine 107 may be in contact with the flow path 104, and the drive unit of the fluid machine 107 may be removable from the substrate.

The flow paths 103, 104, and 105 may have a structure in which the inside can be closed from the outside air. The closed space including the inside of the flow paths 103, 104, and 105 may have a configuration in which gases, viruses, microorganisms, impurities and the like are not exchanged with the outside. The flow paths 103, 104, and 105 may be embedded and enclosed in a non-gas-permeable substance. At least a part of the flow paths 103, 104, and 105 may be provided on a member such as a plate. At least a part of the flow paths 103, 104, and 105 may be formed by carving into a member. At least a part of the flow paths 103, 104, and 105 may be carved into a member and formed by superimposing recesses.

The fluid machine 106 moves the medium in the medium container 101 into the mixing tank 95 through the flow paths 103 and 105. In addition, the fluid machine 107 moves the medium in the medium container 102 into the mixing tank 95 through the flow paths 104 and 105. The fluid machine 106 may quantitatively move the medium in the medium container 101 into the mixing tank 95. The fluid machine 107 may quantitatively move the reagent diluting solution in the medium container 102 into the mixing tank 95. In the case where the medium is transported, each of the medium containers 101 and 102 may contract its volume. Each of the medium containers 101 and 102 may actively contract its volume or may passively contract its volume with aspiration power from the flow paths 103 and 104.

In the mixing tank 95, the factor, the reagent and the medium are mixed. The amounts of the factor and the reagent may be very small, but, In the case where the medium is mixed in, the volume may increase, and supply to the cell culture vessel 22 may be facilitated.

The plurality of medium containers 101 and 102 may store different mediums. For example, depending on the number of times the reagent and the factor are transported from the mixing tank 95 to the cell culture vessel 22, different mediums may be transported from any of the plurality of medium containers 101 and 102 to the mixing tank 95. In addition, for example, depending on the timing at which the reagent and the factor are transported from the mixing tank 95 to the cell culture vessel 22, different mediums may be transported from any of the plurality of medium containers 101 and 102 to the mixing tank 95. For example, in the case where a factor is introduced into cells in the cell culture vessel 22 to change the cells from a first state to a second state, in the initial stage of introducing a factor, the medium suitable for the cells in the first state is supplied from the medium container 101 to the mixing tank 95, and in the later stage of introducing a factor, the medium suitable for the cells in the second state may be supplied from the medium container 102 to the mixing tank 95.

As shown in FIG. 1 and FIG. 2, a flow path 108 for transporting the factor and the reagent from the mixing tank 95 to the cell culture vessel 22 is connected to the mixing tank 95. A fluid machine 109 for moving the fluid in the flow path 108 may be provided in the flow path 108.

The fluid machine 109 may include a pump head and a drive unit that drives the pump head. The flow path 108 may be provided on a substrate, the pump head of the fluid machine 109 may be in contact with the flow path 108, and the drive unit of the fluid machine 109 may be removable from the substrate.

The flow path 108 may have a structure in which the inside can be closed from the outside air. The closed space including the inside of the flow path 108 may have a configuration in which gases, viruses, microorganisms, impurities and the like are not exchanged with the outside. The flow path 108 may be embedded and enclosed in a non-gas-permeable substance. At least a part of the flow path 108 may be provided on a member such as a plate. At least a part of the flow path 108 may be formed by carving into a member. At least a part of the flow path 108 may be carved into a member and formed by superimposing recesses.

The fluid machine 109 moves the factor and the reagent in the mixing tank 95 into the cell culture vessel 22 through the flow path 108. The fluid machine 109 may quantitatively move the factor and the reagent in the mixing tank 95 into the cell culture vessel 22. The fluid machine 109 may transport the reagent and the factor from the mixing tank 95 to the cell culture vessel 22 a predetermined number of times. In addition, the fluid machine 109 may transport the reagent and the factor from the mixing tank 95 to the cell culture vessel 22 at a predetermined timing. In the case where the factor and the reagent are transported, the mixing tank 95 may contract its volume. The mixing tank 95 may actively contract its volume or may passively contract its volume with aspiration power from the flow path 108.

The cells in the cell culture vessel 22 come into contact with the factor and the reagent, and the factor is introduced into the cells. In the case where the factor and the reagent in the mixing tank 95 are quantitatively moved in the cell culture vessel 22, the factor is quantitatively introduced into the cells. In the case where the factor and the reagent in the mixing tank 95 are moved into the cell culture vessel 22 a predetermined number of times, the factor is introduced into the cells a predetermined number of times. In the case where the factor and the reagent in the mixing tank 95 are moved into the cell culture vessel 22 at a predetermined timing, the factor is introduced into cells at a predetermined timing.

A medium container 32, which is a fluid container for storing a medium suitable for cells into which the factor has been introduced, is connected to the cell culture vessel 22, for example, through a flow path 31. In the case where cells into which the factor has been introduced are induced into stem cells, the medium container 32 stores a stem cell medium. In the case where the cells to which the factor has been introduced are induced into somatic cells such as differentiated cells, the medium container 32 stores a somatic cell medium. The medium stored in the medium container 32 may be a gel or a liquid.

The medium container 32 may have a structure in which the inside can be closed from the outside air. The closed space including the inside of the medium container 32 may have a configuration in which gases, viruses, microorganisms, impurities and the like are not exchanged with the outside. The medium container 32 may be embedded and enclosed in a non-gas-permeable substance. At least a part of the medium container 32 may be provided on a member such as a plate. At least a part of the medium container 32 may be formed by carving into a member. At least a part of the medium container 32 may be carved into a member and formed by superimposing recesses. The medium container 32 can change its volume. In this case, for example, the medium container 32 includes a syringe for storing a fluid and a plunger which is inserted into the syringe and movable in the syringe, and the volume for storing the fluid in the syringe can be changed by moving the plunger. Alternatively, the medium container 32 may be a flexible bellows or bag.

The medium container 32 and the flow path 31 may be connected by a connector. The flow path 31 may have a structure in which the inside can be closed from the outside air. The closed space including the inside of the flow path 31 may have a configuration in which gases, viruses, microorganisms, impurities and the like are not exchanged with the outside. The flow path 31 may be embedded and enclosed in a non-gas-permeable substance. At least a part of the flow path 31 may be provided on a member such as a plate. At least a part of the flow path 31 may be formed by carving into a member. At least a part of the flow path 31 may be carved into a member and formed by superimposing recesses. A fluid machine 33 such as a pump for moving the fluid in the flow path 31 may be provided in the flow path 31. A valve other than the fluid machine may not be provided in the flow path 31.

The fluid machine 33 may include a pump head and a drive unit that drives the pump head. The flow path 31 may be provided on a substrate, the pump head of the fluid machine 33 may be in contact with the flow path 31, and the drive unit of the fluid machine 33 may be removable from the substrate.

A temperature adjusting device configured to adjust the temperature of the medium in the medium container 32 may be provided at the medium container 32.

Figure 6:
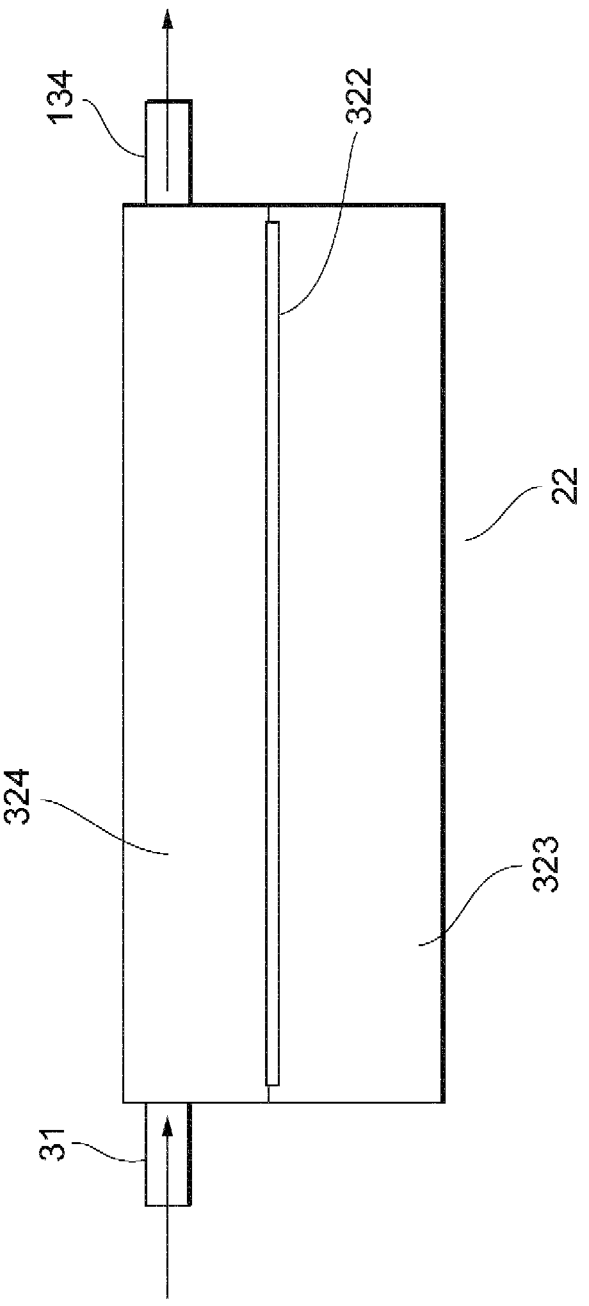
FIG. 6 is a schematic cross-sectional view of a cell culture vessel according to an embodiment.
Figure 7:
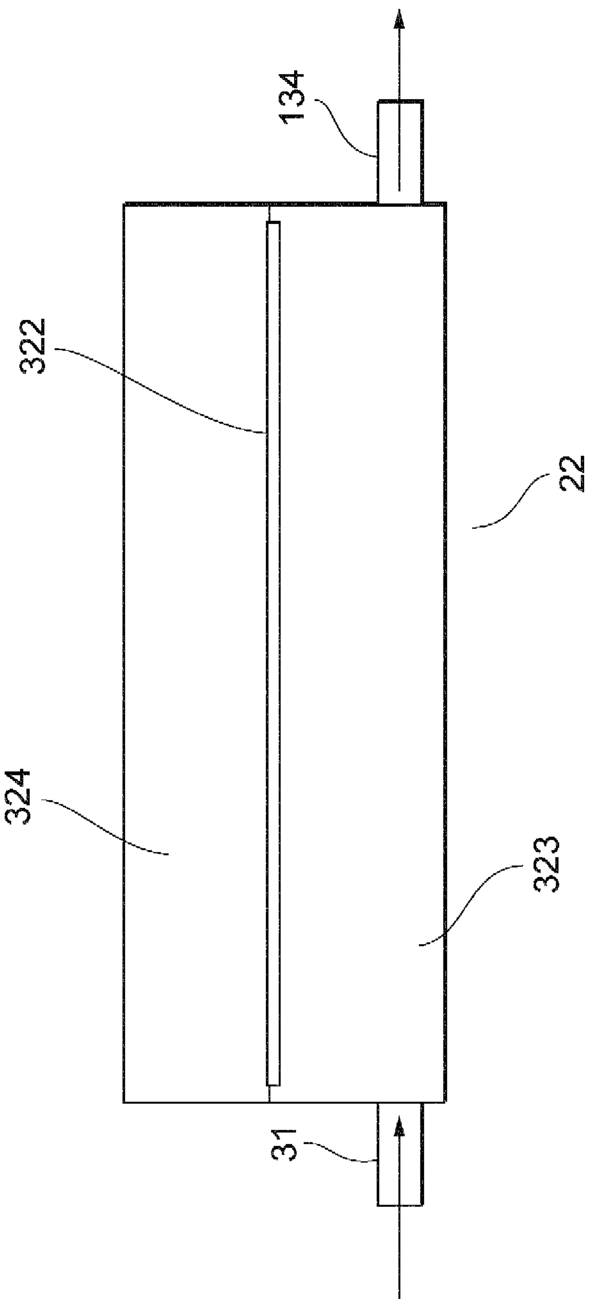
FIG. 7 is a schematic cross-sectional view of a cell culture vessel according to an embodiment.

After a predetermined time has elapsed since the factor is introduced into cells, the fluid machine 33 moves the medium in the medium container 32 into the cell culture vessel 22 through the flow path 31. As shown in FIG. 6, the medium supplied from the medium container 32 may be put into a section 324 which is in contact with a section 323 in which there are cells and in which there are no cells among sections separated by a medium component permeable member 322 in the cell culture vessel 22. Alternatively, as shown in FIG. 7, the stem cell medium may be put into the section 323 in which there are no cells on the lower side in the direction of gravity among sections separated by the medium component permeable member 322 in the cell culture vessel 22. In this case, there are cells in the section 324 on the upper side in the direction of gravity. The medium container 32 that has aspirated the medium from the inside may contract its volume. Here, the medium container 32 may actively contract its volume or may passively contract its volume.

In the case where the medium is transported from the medium container 32 shown in FIG. 1 and FIG. 2 into the cell culture vessel 22, the excess fluid in the cell culture vessel 22 may move, for example, into the storage tank 130, and the storage tank 130 may expand its volume and receive the fluid that has moved from the inside of the cell culture vessel 22 through the flow path 132 or the flow path 134. The flow path 132 or the flow path 134 may be connected to a section in which there are no cells among sections separated by the medium component permeable member in the cell culture vessel 22.

Alternatively, the flow path 132 or the flow path 134 may be in contact with a section in which there are cells among sections separated by the medium component permeable member in the cell culture vessel 22. In this case, excess cells in the cell culture vessel 22 may be transported to the storage tank 130 through the flow path 132 or the flow path 134.

Among sections separated by the medium component permeable member in the cell culture vessel 22, the medium in the section in which there are cells and the medium in the section in which there are no cells exchange medium components and waste products due to, for example, osmotic pressure. For example, a semipermeable membrane, a mesh, or a hollow fiber membrane can be used as the culture component permeable member. The semipermeable membrane includes a dialysis membrane.

In the case where the culture component permeable member is a semipermeable membrane, the molecular weight cutoff of the semipermeable membrane is, for example, 0.1 KDa or more, 10 KDa or more, or 50 KDa or more. Examples of semipermeable membranes include cellulose ester, ethyl cellulose, cellulose esters, regenerated cellulose, polysulfone, polyacrylonitrile, polymethylmethacrylate, ethylene vinyl alcohol copolymers, polyester polymer alloys, polycarbonate, polyamide, cellulose acetate, cellulose diacetate, cellulose triacetate, cuprammonium rayon, saponified cellulose, hemophan membranes, phosphatidylcholine membranes, and vitamin E coating films.

In the case where the culture component permeable member is a mesh, the mesh has smaller pores than the cells cultured in the cell culture vessel 22. The material of the mesh is, for example, a resin or a metal, but it is not particularly limited. The surface of the culture component permeable member may be non-cell-adhesive.

In the case where the culture component permeable member is a hollow fiber membrane, the hollow fiber membrane has smaller pores than the cells cultured in the cell culture vessel 22. For example, cells may be cultured inside the hollow fiber membrane.

In the case where cells are cultured in the cell culture vessel 22, the fluid machine 33 may move the medium in the medium container 32 into the cell culture vessel 22 through the flow path 31 at a predetermined timing. The storage tank 130 may receive the excess medium used in the cell culture vessel 22 due to inflow of a new medium. The fluid machine 33 may control the amount of the medium transported according to, for example, the state of the medium, the state of the cell mass in the medium, the number of cells, the number of cell masses, the turbidity of the medium, and the change in pH, and may start and end transfer of the medium.

A dissociation reagent container 120 for storing a dissociation reagent for detaching the cells cultured in the cell culture vessel 22 from the cell culture vessel 22 may be connected to the cell culture vessel 22. Here, the dissociation reagent may be used to crush floating cell masses.

The dissociation reagent container 120 may have a structure in which the inside can be closed from the outside air. The closed space including the inside of the dissociation reagent container 120 may have a configuration in which gases, viruses, microorganisms, impurities and the like are not exchanged with the outside. The dissociation reagent container 120 may be embedded and enclosed in a non-gas-permeable substance. At least a part of the dissociation reagent container 120 may be provided on a member such as a plate. At least a part of the dissociation reagent container 120 may be formed by carving into a member. At least a part of the dissociation reagent container 120 may be carved into a member and formed by superimposing recesses. The dissociation reagent container 120 can change its volume. In this case, for example, the dissociation reagent container 120 includes a syringe for storing a fluid and a plunger which is inserted into the syringe and movable in the syringe, and the volume for storing the fluid in the syringe can be changed by moving the plunger. Alternatively, the dissociation reagent container 120 may be a flexible bellows or bag.

A flow path 121 for transporting at least the dissociation reagent from the dissociation reagent container 120 to the cell culture vessel 22 is connected to the dissociation reagent container 120. The dissociation reagent container 120 and the flow path 121 may be connected by a connector. A fluid machine 122 for moving the fluid in the flow path 121 may be provided in the flow path 121. A valve other than the fluid machine may not be provided in the flow path 121.

The fluid machine 122 may include a pump head and a drive unit that drives the pump head. The flow path 121 may be provided on a substrate, the pump head of the fluid machine 122 may be in contact with the flow path 121, and the drive unit of the fluid machine 122 may be removable from the substrate.

The flow path 121 may have a structure in which the inside can be closed from the outside air. The closed space including the inside of the flow path 121 may have a configuration in which gases, viruses, microorganisms, impurities and the like are not exchanged with the outside. The flow path 121 may be embedded and enclosed in a non-gas-permeable substance. At least a part of the flow path 121 may be provided on a member such as a plate. At least a part of the flow path 121 may be formed by carving into a member. At least a part of the flow path 121 may be carved into a member and formed by superimposing recesses.

The fluid machine 122 moves the dissociation reagent in the dissociation reagent container 120 into the cell culture vessel 22 through the flow path 121. The fluid machine 122 may quantitatively move the dissociation reagent in the dissociation reagent container 120 into the cell culture vessel 22. In the case where the dissociation reagent is transported, the dissociation reagent container 120 may contract its volume. The dissociation reagent container 120 may actively contract its volume or may passively contract its volume with aspiration power from the flow path 121.

After the detached cells are moved from the cell culture vessel 22 to the flow path, at least some of the cells may be returned to the cell culture vessel 22 and the cells may be subcultured. Here, in the case of suspended-culture, cells can be subcultured without detachment. A structure for dividing cell masses may be provided in the flow path through which cells are received from the cell culture vessel 22 and the cells are returned to the cell culture vessel 22 again. The cell masses may be divided into small cell masses or may be divided into single cells.

A cryopreservation solution container 123 for storing a cryopreservation solution for cryopreserving cells cultured in the cell culture vessel 22 may be connected to the cell culture vessel 22.

The cryopreservation solution container 123 may have a structure in which the inside can be closed from the outside air. The closed space including the inside of the cryopreservation solution container 123 may have a configuration in which gases, viruses, microorganisms, impurities and the like are not exchanged with the outside. The cryopreservation solution container 123 may be embedded and enclosed in a non-gas-permeable substance. At least a part of the cryopreservation solution container 123 may be provided on a member such as a plate. At least a part of the cryopreservation solution container 123 may be formed by carving into a member. At least a part of the cryopreservation solution container 123 may be carved into a member and formed by superimposing recesses. The cryopreservation solution container 123 can change its volume. In this case, for example, the cryopreservation solution container 123 includes a syringe for storing a fluid and a plunger which is inserted into the syringe and movable in the syringe, and the volume for storing the fluid in the syringe can be changed by moving the plunger. Alternatively, the cryopreservation solution container 123 may be a flexible bellows or bag.

A flow path 124 for transporting at least the cryopreservation solution from the cryopreservation solution container 123 to the cell culture vessel 22 is connected to the cryopreservation solution container 123. The cryopreservation solution container 123 and the flow path 124 may be connected by a connector. A fluid machine 125 for moving the fluid in the flow path 124 may be provided in the flow path 124. A valve other than the fluid machine may not be provided in the flow path 124.

The fluid machine 125 may include a pump head and a drive unit that drives the pump head. The flow path 124 may be provided on a substrate, the pump head of the fluid machine 125 may be in contact with the flow path 124, and the drive unit of the fluid machine 125 may be removable from the substrate.

The flow path 124 may have a structure in which the inside can be closed from the outside air. The closed space including the inside of the flow path 124 may have a configuration in which gases, viruses, microorganisms, impurities and the like are not exchanged with the outside. The flow path 124 may be embedded and enclosed in a non-gas-permeable substance. At least a part of the flow path 124 may be provided on a member such as a plate. At least a part of the flow path 124 may be formed by carving into a member. At least a part of the flow path 124 may be carved into a member and formed by superimposing recesses.

The fluid machine 125 moves the cryopreservation solution in the cryopreservation solution container 123 into the cell culture vessel 22 in which cells float through the flow path 124. The fluid machine 125 may quantitatively move the cryopreservation solution in the cryopreservation solution container 123 into the cell culture vessel 22. In the case where the cryopreservation solution is transported, the cryopreservation solution container 123 may contract its volume. The cryopreservation solution container 123 may actively contract its volume or may passively contract its volume with aspiration power from the flow path 124.

A cell freezing container 126 for cryopreserving cells may be connected to the cell culture vessel 22.

The cell freezing container 126 may have a structure in which the inside can be closed from the outside air. The closed space including the inside of the cell freezing container 126 may have a configuration in which gases, viruses, microorganisms, impurities and the like are not exchanged with the outside. The cell freezing container 126 may be embedded and enclosed in a non-gas-permeable substance. At least a part of the cell freezing container 126 may be provided on a member such as a plate. At least a part of the cell freezing container 126 may be formed by carving into a member. At least a part of the cell freezing container 126 may be carved into a member and formed by superimposing recesses. The cell freezing container 126 can change its volume. In this case, for example, the cell freezing container 126 includes a syringe for storing a fluid and a plunger which is inserted into the syringe and movable in the syringe, and the volume for storing the fluid in the syringe can be changed by moving the plunger. Alternatively, the cell freezing container 126 may be a flexible bellows or bag.

A flow path 127 for transporting at least the cells and the cryopreservation solution from the cell culture vessel 22 into the cell freezing container 126 is connected to the cell freezing container 126. A structure for dividing cell masses may be provided in the flow path 127. The cell freezing container 126 and the flow path 127 may be connected by a connector. A fluid machine 128 for moving the fluid in the flow path 127 may be provided in the flow path 127. A valve other than the fluid machine may not be provided in the flow path 127.

The fluid machine 128 may include a pump head and a drive unit that drives the pump head. The flow path 127 may be provided on a substrate, the pump head of the fluid machine 128 may be in contact with the flow path 127, and the drive unit of the fluid machine 128 may be removable from the substrate.

The flow path 127 may have a structure in which the inside can be closed from the outside air. The closed space including the inside of the flow path 127 may have a configuration in which gases, viruses, microorganisms, impurities and the like are not exchanged with the outside. The flow path 127 may be embedded and enclosed in a non-gas-permeable substance. At least a part of the flow path 127 may be provided on a member such as a plate. At least a part of the flow path 127 may be formed by carving into a member. At least a part of the flow path 127 may be carved into a member and formed by superimposing recesses.

The fluid machine 128 moves the cells and the cryopreservation solution in the cell culture vessel 22 into the cell freezing container 126 through the flow path 127. The fluid machine 128 may quantitatively move the cells and the cryopreservation solution in the cell culture vessel 22 into the cell freezing container 126. In the case where the cells and the cryopreservation solution are received, the cell freezing container 126 may expand its volume. The cell freezing container 126 may actively expand its volume, and may passively expand its volume according to the pressure from the flow path 127.

The erythrocyte removal device 100 and the cell culture device 200 according to the embodiment may be provided on one substrate. Respective components of the erythrocyte removal device 100 and the cell culture device 200 may be formed by carving into the substrate. Respective components of the erythrocyte removal device 100 and the cell culture device 200 may be formed by combining recesses carved at the same position on at least two substrates. The erythrocyte removal device 100 and the cell culture device 200 may be enclosed so that respective components of the erythrocyte removal device 100 and the cell culture device 200 do not come into contact with the outside air.

The erythrocyte removal device 100 and the cell culture device 200 according to the embodiment may include a substrate on which a drive unit of a fluid machine is provided and a substrate on which a flow path and the like are provided. The erythrocyte removal device 100 and the cell culture device 200 may be formed by superimposing the substrate on which the drive unit of the fluid machine is provided and the substrate on which the flow path and the like are provided.

According to the findings of the inventors, since cells can be cultured in a closed space that is completely closed, it is not necessary to actively supply carbon dioxide gas, nitrogen gas, oxygen gas or the like into the cell culture vessel 22. Therefore, the cell culture vessel 22 may not be disposed in a $CO_2$ incubator. In addition, since cells, microorganisms, viruses, dust and the like present outside the cell culture vessel 22 do not enter the sealed cell culture vessel 22, the cleanliness in the cell culture vessel 22 is maintained. Therefore, the cell culture vessel 22 may not be disposed in a clean room. However, supply of carbon dioxide gas, nitrogen gas, oxygen gas and the like into the closed system in which there are cells is not necessarily hindered.

According to the erythrocyte removal device 100 of the embodiment, for example, since blood is treated in a completely closed system, it is possible to reduce a risk of infection due to blood leakage from the device. According to the cell culture device 200 of the embodiment, for example, since cells are cultured in a completely closed system, it is possible to reduce a risk of cross-contamination due to leakage of cells and factors from the culture device. In addition, for example, even if cells are infected with viruses such as HIV hepatitis viruses, it is possible to reduce a risk of infection with an operator due to cell leakage. In addition, it is possible to reduce a risk of the medium in the cell culture vessel contaminating the air outside the cell culture vessel with bacteria, viruses, molds and the like. In addition, according to the cell culture vessel of the embodiment, it is possible to culture cells without using a $CO_2$ incubator. Here, the closed system may indicate a system in which microorganisms such as bacteria and viruses, and dust do not enter from the outside. The closed system may have a configuration in which a gas is allowed to enter from the outside or a gas cannot enter.

(Other Embodiments)

While the present invention has been described above with reference to the embodiment, the descriptions and drawings that form some of the disclosure should not be understood as limiting the invention. Those skilled in the art can clearly understand various alternative embodiments, embodiments and operational techniques from this disclosure. For example, the cells transported to the cell culture vessel 22 shown in FIG. 1 are not limited to mononuclear cells. The cells transported to the cell culture vessel 22 may be stem cells, fibroblasts, or other somatic cells. The cells transported to the cell culture vessel 22 are arbitrary.

EXAMPLES

Example 1

In this example, an example in which cells could be cultured in a completely closed environment without medium replacement and gas exchange is shown. A growth factor was added to a medium (StemSpan H3000, registered trademark, STEMCELL Technologies Inc.), and deacylated gellan gum was additionally added to the medium to prepare a gel medium.

The prepared gel medium was put into a 15 mL tube and $2\times10^5$ blood cells were seeded in the gel medium. Then, the 15 mL tube was placed in a $CO_2$ incubator, and blood cells (mononuclear cells) were cultured for 7 days. Then, a Sendai virus vector containing OCT3/4, SOX2, KLF4, and cMYC was added to the gel medium so that the multiplicity of infection (MOI) was 10.0, and the blood cells were infected with Sendai viruses.

After Sendai viruses were added to the gel medium, 15 mL of the gelled stem cell medium (DMEM/F12 containing 20% KnockOut SR (registered trademark, ThermoFisher SCIENTIFIC)) was added to the gel medium, and then 15 mL of the medium containing cells infected with Sendai viruses was put into a sealable cell culture vessel, and the gel medium was injected into the cell culture vessel. Then, the inside of the cell culture vessel was sealed such that gas exchange did not completely occur between the inside and the outside of the cell culture vessel.

Suspended-culture of the cells into which the initialization factor was introduced started in the cell culture vessel. Then, once every two days, 2 mL of the gel medium in a medium retention tank 40 was replaced with 2 mL of a new gel medium.

Figure 10:
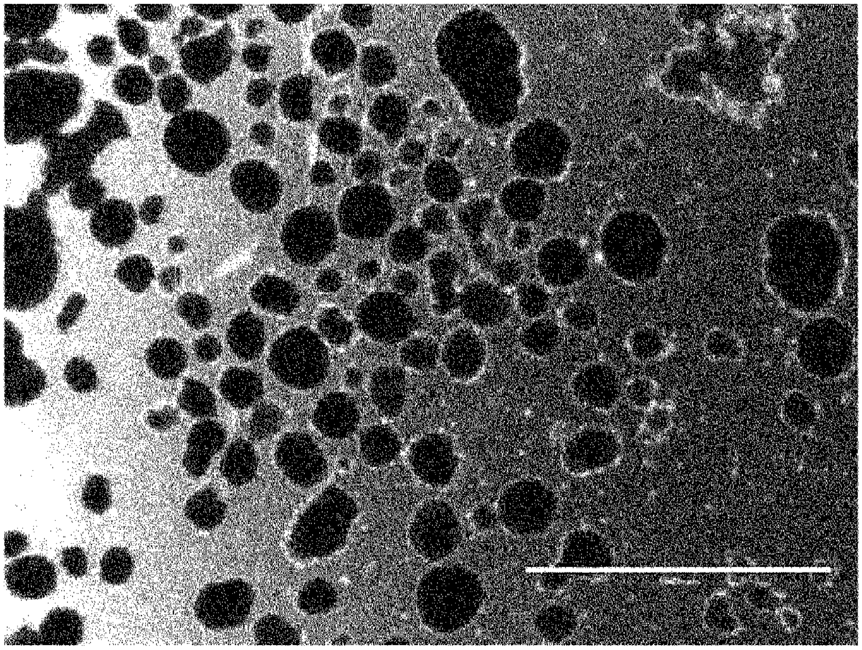
FIG. 10 shows a microscopic image of cell masses according to Example 1.
Figure 11:
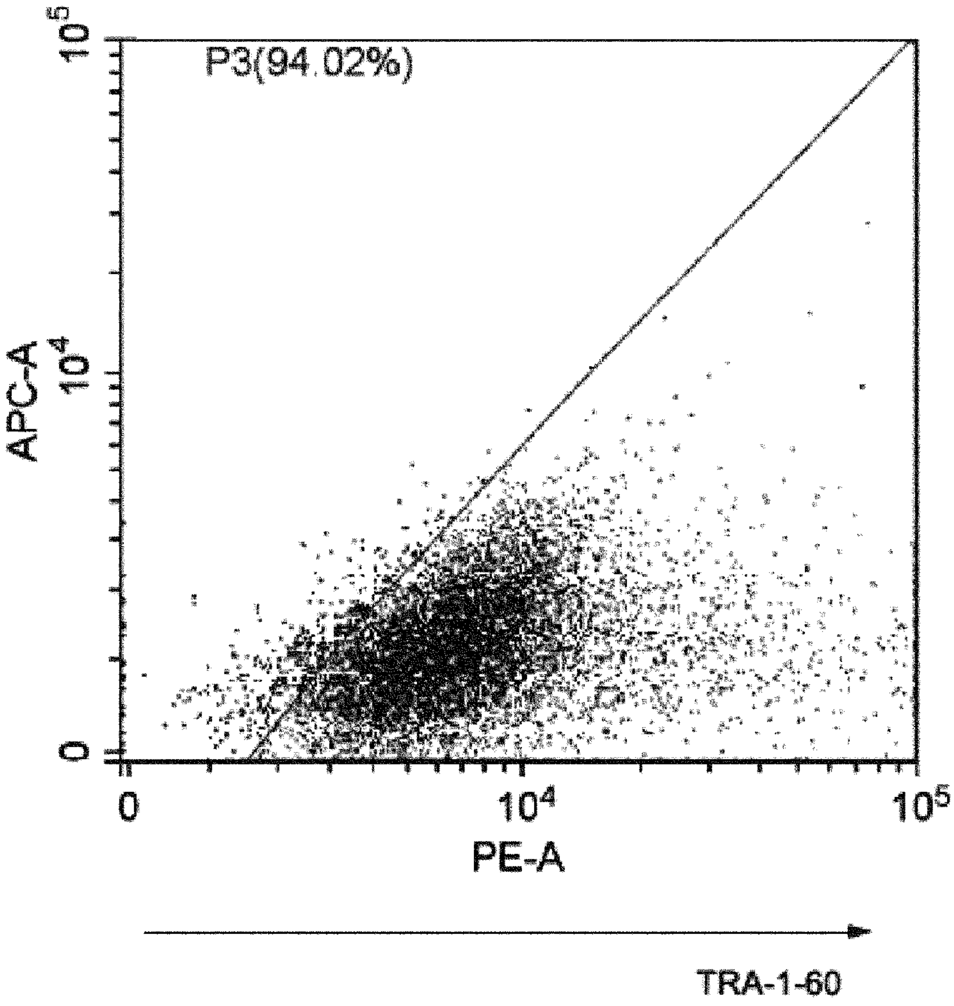
FIG. 11 is a histogram showing the results of flow cytometry of iPS cells according to Example 1.

After 15 days, when the cells were observed under a microscope, as shown in FIG. 10, it was confirmed that ES cell-like colonies were formed. In addition, when cells were fixed using 4%-paraformaldehyde, and the expression level of cell surface antigen TRA-1-60 in the fixed cells was measured using a flow cytometer, as shown in FIG. 11, it was confirmed that 90% or more of the cells were TRA-1-60 positive, and the cells were almost completely reprogrammed. Therefore, it was found that, in a completely closed environment, iPS cells could be induced from somatic cells other than stem cells without medium replacement and gas exchange.

Example 2

Figure 12:
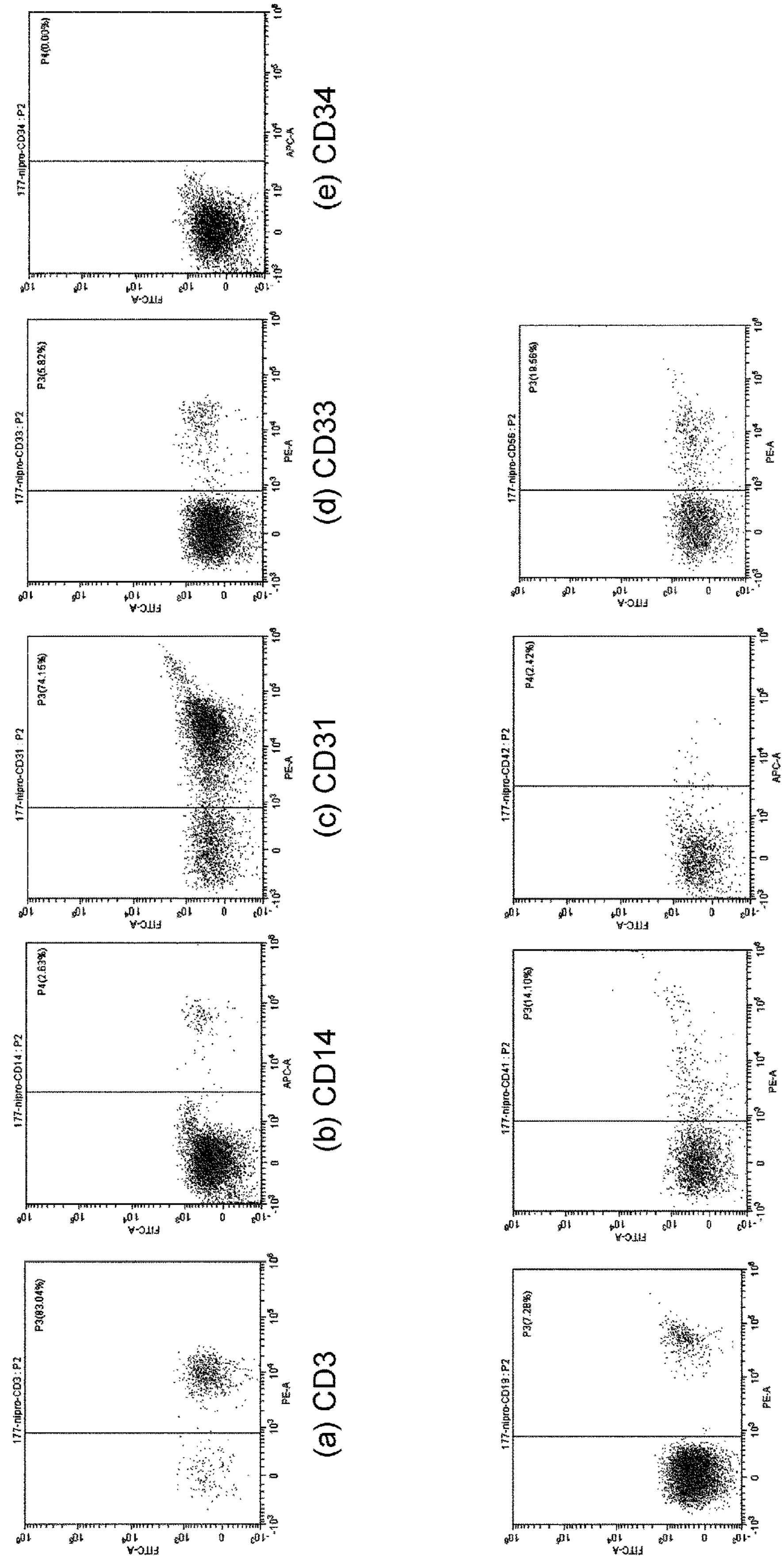
FIG. 12 shows the analysis results of fluorescence-activated cell sorting according to Example 2.

Blood was treated with a erythrocyte precipitating agent to obtain treated blood from which erythrocytes were at least partially removed. The treated blood was treated with surface cell marker antibodies and analyzed by fluorescence-activated cell sorting (FACS), and the results are shown in FIG. 12. The treated blood contained CD3 positive cells, CD14 positive cells, CD31 positive cells, CD33 positive cells, CD34 positive cells, CD19 positive cells, CD41 positive cells, CD42 positive cells, and CD56 positive cells.

Figure 13:
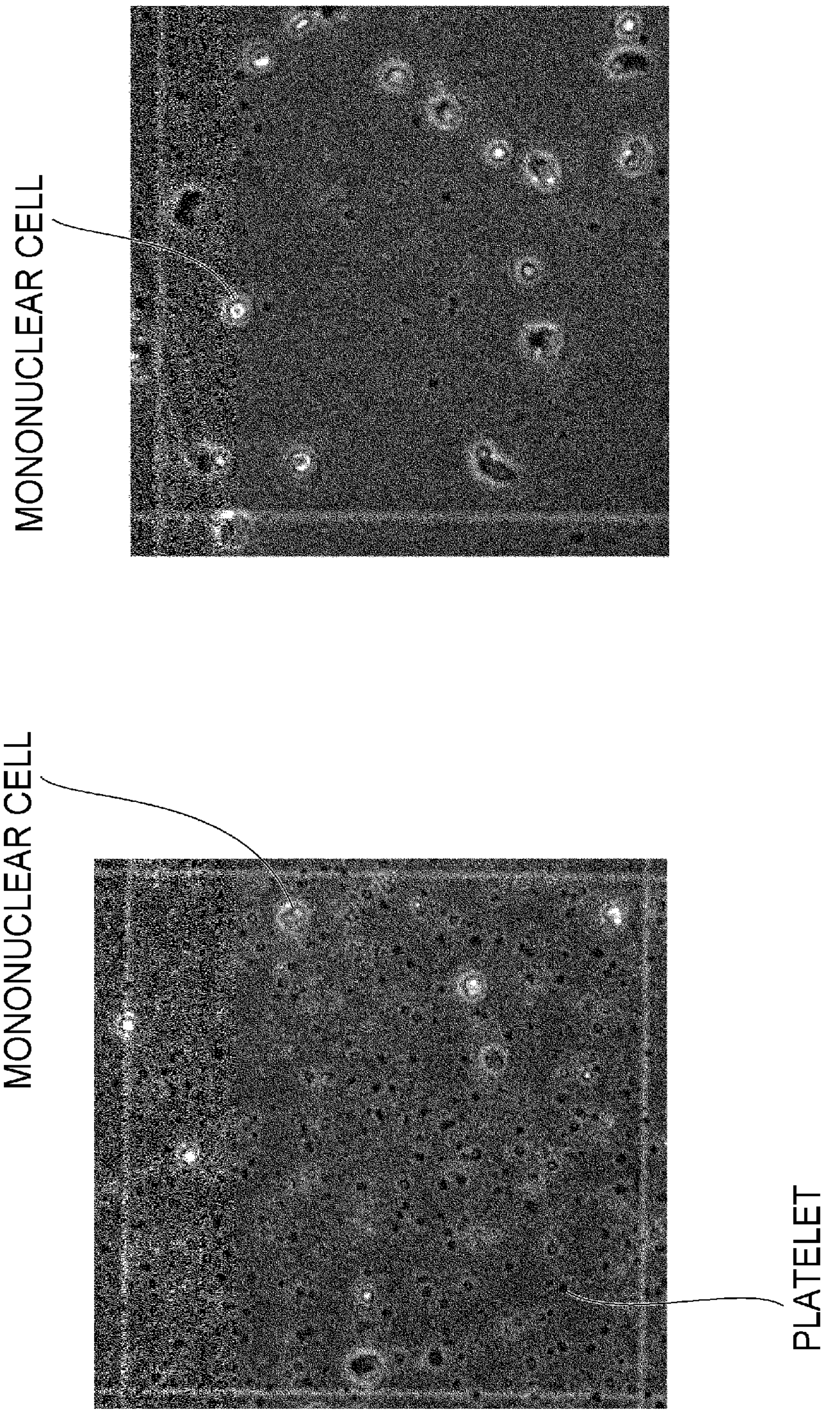
FIG. 13(*a*) shows a microscopic image of treated blood before it is put into a mononuclear cell collector according to Example 2 and FIG. 13(*b*) shows a microscopic image of a solution containing mononuclear cells collected from the mononuclear cell collector.
Figure 14:
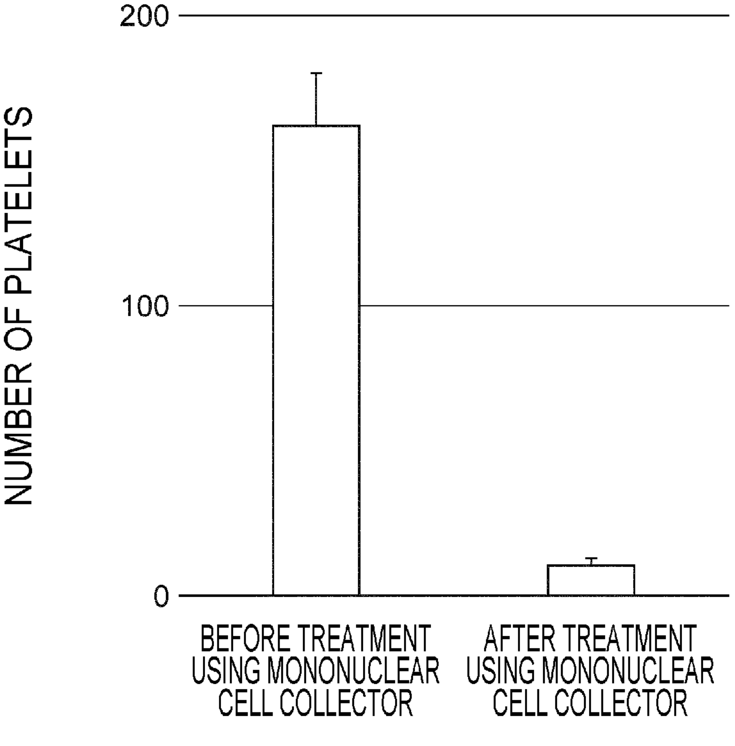
FIG. 14 is a graph showing the number of platelets in treated blood before it is put into the mononuclear cell collector according to Example 2 and the number of platelets in a solution containing mononuclear cells collected from the mononuclear cell collector.

The treated blood from which erythrocytes were at least partially removed was put into a mononuclear cell collector shown in FIG. 3, and diluted with a buffer solution, and the supernatant was removed. Then, the mononuclear cells were collected from the mononuclear cell collector. As shown in FIG. 13(*a*), the treated blood before it was put into the mononuclear cell collector contained a large number of platelets. On the other hand, as shown in FIG. 13(*b*), the platelets were almost removed from the solution containing mononuclear cells collected from the mononuclear cell collector. FIG. 14 shows a graph showing the number of platelets in the treated blood before it was put into the mononuclear cell collector and the number of platelets in the solution containing the mononuclear cells collected from the mononuclear cell collector in the same area.

Figure 15:
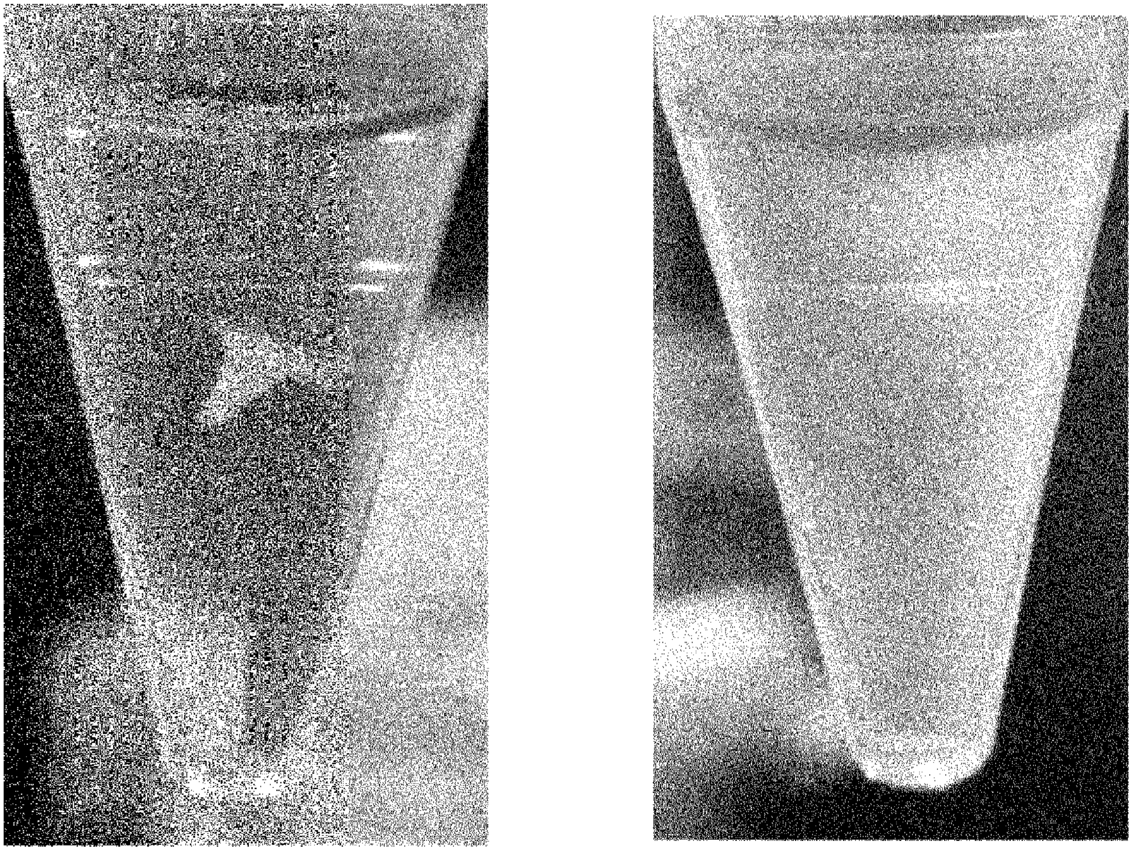
FIG. 15(*a*) shows an image of a culture solution containing treated blood containing platelets before it is put into the mononuclear cell collector according to Example 2 and FIG. 15(*b*) shows an image of a culture solution containing a solution containing mononuclear cells from which platelets are removed.

When the treated blood containing platelets before it was put into the mononuclear cell collector was put into the culture solution, as shown in FIG. 15(*a*), aggregation occurred. On the other hand, when the solution containing mononuclear cells from which platelets had been removed, which were collected from the mononuclear cell collector, was put into the culture solution, as shown in FIG. 15(*b*), no aggregation occurred.

Reference Signs List

| | |
|---|---|
| 11 | Erythrocyte remover |
| 15 | Mononuclear cell collector |
| 17 | Flow path |
| 18 | Fluid machine |
| 19 | Flow path |
| 20 | Mononuclear cell aspiration device |
| 21 | Fluid machine |
| 22 | Cell culture vessel |
| 23 | Flow path |
| 24 | Fluid machine |
| 25 | Medium container |
| 31 | Flow path |
| 32 | Medium container |
| 33 | Fluid machine |
| 34 | Flow path |
| 35 | Coating agent container |
| 36 | Fluid machine |
| 40 | Medium retention tank |
| 50 | Blood container |
| 51 | Flow path |
| 52 | Fluid machine |
| 53 | Erythrocyte treatment agent container |
| 54 | Flow path |
| 55 | Fluid machine |
| 56 | Flow path |
| 57 | Mixer |
| 58 | Flow path |
| 60 | Flow path |
| 61 | Dilution liquid container |
| 62 | Fluid machine |

-continued

Reference Signs List

| | |
|---|---|
| 81 | Factor container |
| 82 | Reagent container |
| 83 | Diluting solution container |
| 84 | Factor diluting container |
| 85 | Flow path |
| 86 | Flow path |
| 87 | Flow path |
| 88 | Fluid machine |
| 89 | Reagent diluting container |
| 90 | Flow path |
| 91 | Flow path |
| 92 | Flow path |
| 93 | Fluid machine |
| 94 | Fluid machine |
| 95 | Mixing tank |
| 96 | Flow path |
| 97 | Flow path |
| 98 | Flow path |
| 99 | Fluid machine |
| 100 | Erythrocyte removal device |
| 101 | Medium container |
| 102 | Medium container |
| 103 | Flow path |
| 104 | Flow path |
| 105 | Flow path |
| 106 | Fluid machine |
| 107 | Fluid machine |
| 108 | Flow path |
| 109 | Fluid machine |
| 115 | Opening |
| 116 | Opening |
| 117 | Flow path |
| 120 | Dissociation reagent container |
| 121 | Flow path |
| 122 | Fluid machine |
| 123 | Cryopreservation solution container |
| 124 | Flow path |
| 125 | Fluid machine |
| 126 | Cell freezing container |
| 127 | Flow path |
| 128 | Fluid machine |
| 130 | Storage tank |
| 131 | Flow path |
| 132 | Flow path |
| 133 | Fluid machine |
| 134 | Flow path |
| 135 | Flow path |
| 137 | Flow path |
| 187 | Fluid machine |
| 200 | Cell culture device |
| 222 | Housing |
| 223 | Housing |
| 322 | Medium component permeable member |
| 323 | Section |
| 324 | Section |

What is claimed is:

1. A cell culture device, comprising:

a cell culture vessel for culturing cells;

a factor container for storing a factor;

a factor diluting container connected to the factor container;

a reagent container for storing a reagent for introducing the factor into the cells;

a reagent diluting container connected to the reagent container;

a diluting solution container for storing a diluting solution, the diluting solution container connected to the factor diluting container and the reagent diluting container;

a first flow path connected to the factor diluting container, the reagent diluting container, and the cell culture vessel for transporting the factor diluted with the diluting solution and the reagent diluted with the diluting solution from the factor diluting container and the reagent diluting container, respectively, to the cell culture vessel;

a mixing tank provided at the first flow path for mixing the factor diluted with the diluting solution and the reagent diluted with the diluting solution;

a medium container connected to the mixing tank for storing a medium supplied to the mixing tank; and a cryopreservation solution container for storing a cryopreservation solution for cryopreserving the cells, the cryopreservation solution container directly connected to the cell culture vessel by a second flow path such that the cryopreservation solution is directly transferred from the cryopreservation solution container to the cell culture vessel via the second flow path, wherein the cell culture device is configured such that the cells come into contact with the factor, the reagent, and the medium in the cell culture vessel only, and that the factor is introduced into the cells in the cell culture vessel.

2. The cell culture device according to claim 1, further comprising a first fluid machine for transporting the factor from the factor container to the factor diluting container.

3. The cell culture device according to claim 1, further comprising a second fluid machine for transporting the reagent from the reagent container to the reagent diluting container.

4. The cell culture device according to claim 1, further comprising a third fluid machine provided between the mixing tank and the cell culture vessel for transporting contents of the mixing tank to the cell culture vessel.

5. The cell culture device according to claim 1, further comprising a second medium container connected to the mixing tank and storing a second medium to be supplied to the mixing tank.

6. The cell culture device according to claim 1, wherein an inside of the cell culture vessel, an inside of the factor container, an inside of the reagent container, and an inside of the first flow path are able to be closed from outside air.

7. The cell culture device according to claim 1, wherein an inside of the mixing tank is able to be closed from outside air.

8. The cell culture device according to claim 1, wherein an inside of the diluting solution container is able to be closed from outside air.

9. The cell culture device according to claim 1, wherein an inside of the medium container is able to be closed from outside air.

10. The cell culture device according to claim 1, wherein a volume of at least one of the factor container and the reagent container is variable.

11. The cell culture device according to claim 1, wherein a volume of the mixing tank is variable.

12. The cell culture device according to claim 1, wherein a volume of the diluting solution container is variable.

13. The cell culture device according to claim 1, wherein a volume of the medium container is variable.

14. The cell culture device according to claim 1, wherein the factor is at least one selected from DNA, RNA, a protein, and a compound.

15. The cell culture device according to claim 1, wherein the cell culture vessel, the factor container, the reagent container, and the first flow path are provided on a vertical plate.

16. The cell culture device according to claim 4, wherein the third fluid machine is a pump.

17. The cell culture device according to claim 1, wherein the cell culture vessel contains cells being cultured therein, the factor container contains at least one selected from the group consisting of DNA, RNA, a protein, and a compound, the reagent container contains a transfection reagent capable of introducing the at least one of the DNA, the RNA, the protein, and the compound into the cells, and the diluting solution container contains phosphate buffered saline (PBS).

* * * * *